Figure 2:
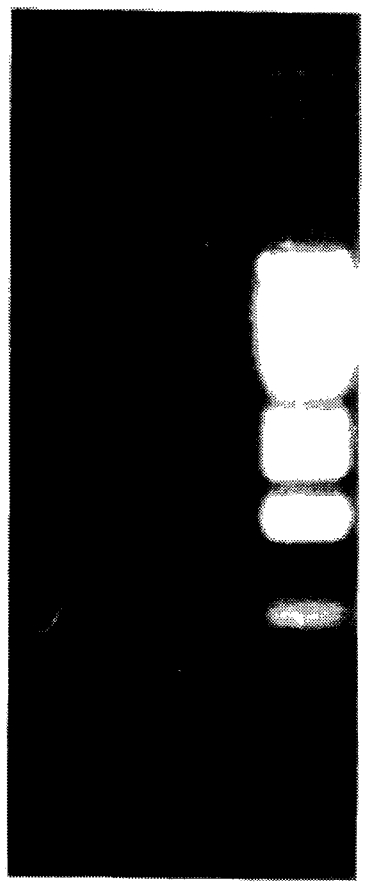

US005567602A

United States Patent [19]
Clark et al.

[11] Patent Number: 5,567,602
[45] Date of Patent: Oct. 22, 1996

[54] RECOMBINANT PRODUCTION OF CHYMASE

[75] Inventors: James M. Clark, San Mateo; Kevin R. Shoemaker; Robert L. Warne, both of San Francisco, all of Calif.

[73] Assignee: Arris Pharmaceutical Corporation, South San Francisco, Calif.

[21] Appl. No.: 929,198

[22] Filed: Aug. 12, 1992

[51] Int. Cl.$^6$ .......................... C12N 15/57; C12N 15/62; C12N 15/09; C12N 15/10

[52] U.S. Cl. .................. 435/226; 435/69.1; 435/69.7; 435/69.8; 435/71.2; 435/172.3; 435/320.1; 435/240.2; 435/252.3; 435/252.33; 935/10; 935/14; 935/29; 935/47; 935/48; 935/70; 935/72; 935/73; 536/23.2

[58] Field of Search ............................. 435/69.1, 69.7, 435/69.8, 71.2, 226, 172.3, 320.1, 240.2, 252.3, 252.33; 935/10, 14, 29, 47, 48, 70, 72, 73; 536/23.2

[56] References Cited

FOREIGN PATENT DOCUMENTS

| WO90/10649 | 9/1990 | WIPO. |
| WO91/13904 | 9/1991 | WIPO. |
| WO92/00374 | 1/1992 | WIPO. |

OTHER PUBLICATIONS

N. K. Puwri "Refolding of recombinant porcine Growth Hormone . . . " FEBS Letts. 292(1/2)187–190 (Nov. 1991).
B. D. Korant et al. "An E. coli expression system which . . . " Biomed. Biochim. Acta. 50(4–6) 643–646 (1991).
L. F. Wang et al. "Expression in E. coli of the Bacillus . . . " Derwent Biotechnology Abstracts 10(16) 105 Abst. No. 91–09529(Aug. 1991).
C. D. O'Connor et al. "Highly Repressible Expression . . . " J. Bacteriology 169(10) 4457–4462 (Oct. 1987).
J. R. Vasquez et al. "An Expression System for Trysin" J. Cell. Biochem. 39: 265–76 (1989).
J. M. Louis et al. "Autoprocessing of the HIV–1 Protease . . . " Eur. J. Biochem 199: 361–369 (1991).
S. J. Busby et al. "Expression of Recombinant Human Plasminoger . . . " J. Biol. Chem. 266(23) 15286–15292 (Aug. 1991).
Chu et al., 1992, "Molecular Cloning and Characterization of Mouse Mast Cell Chymases", Biochimica et Biophysica Acta. 1121:83–87.
Cole et al., 1992, "Isolation and Expression of a Gene Which Encodes a Wall–Associated Proteinase of Coccidioides immitis", Infection Immunity 60:416–427.
Kaiser and Hoskin, 1992, "Expression and Utilization of Chymotrypsin–like but Not Trypsin–like Serine Protease Enzymes by Nonspecific T Killer Cells Activated by Anti–CD3 Monoclonal Antibody", Cellular Immunol. 141:84–98.
Rani et al., 1992 FASEB J., "Total Synthesis and Expression of the Dog Mast Cell Chymase Gene" 6: 1346.

Caughey et al., 1991, "Structure, Chromosomal Assignment, and Deduced Amino Acid Sequence of a Human Gene for Mast Cell Chymase", J. Bio. Chem. 266:12956–12963.
Huang et al., 1991 "Cloning and Structural Analysis of MMCP–1, MMCP–4, and MMCP–5, Three Mouse Mast Cell–Specific Serine Proteases", Eur. J. Immunol. 21:1611–1621.
Kinoshita et al., 1991, "Multiple Determinants for the High Substrate Specificity of an Angiotensin II–forming Chymase from the Human Heart", J. Biol. Chem. 266:19192–19197.
MacDougall et al., 1991, "Cloning and Expression of Protease Genes from Treponema denticola in Escherichia coli", Oral Microbiol. Immunol. 6:270–274.
McNeil et al., 1991 "Molecular Cloning of the Mouse Mast Cell Protease–5 Gene: A Novel Secretory Granule Protease Expressed Early in the Differentiation of Serosal Mast Cells", J. Biol. Chem. 266:20316–20322.
Urata et al. 1991, "Cloning of the Gene and cDNA for Human Heart Chymase", J. Biol. Chem. 266:17173–17179.
Reynolds et al., 1991 "Cloning of the cDNA and Gene of Mouse Mast Cell Protease–6", J. Biol. Chem. 266:3847–3853.
Serafin et al., 1991 "Cloning of the cDNA and Gene for Mouse Mast Cell Protease 4", J. Biol. Chem. 266:1934–1941.
Serafin et al., 1990 "Identification and Molecular Cloning of a Novel Mouse Mucosal Mast Cell Serine Protease", J. Biol. Chem. 265:423–429.
Bishop, 1990, "Gene Expression Using Insect Cells and Viruses", Current Opinion In Biotechnology 1:62–67.
Caughey et al., 1990, "Dog Mast Cell Chymase: Molecular Cloning and Characterization", Biochemistry 29:5166–5171.
Nelson and Siman, 1990, "Clipsin, a Chymotrypsin–like Protease in rat Brain Which Is Irreversibly Inhibited by α–1–Antichymotrypsin", J. Biol. Chem. 265;3836–3843.
Kitts et al., 1990, "Linearization of Baculovirus DNA Enhances the Recovery of Recombinant Virus Expression Vectors", Nucleic Acids Res. 18:5667–5672.

(List continued on next page.)

Primary Examiner—Robert A. Wax
Assistant Examiner—Rebecca Prouty
Attorney, Agent, or Firm—Pennie & Edmonds

[57] ABSTRACT

The instant invention is directed to recombinant production of functionally active chymase. "Functionally active" as used herein refers to the ability to exhibit one or more functional activities of a full-length wild-type chymase protein. In a preferred aspect, a proteolytically inactive chymase fusion protein comprising a functionally active portion of a non-chymase protein joined to the amino-terminus of the chymase protein is produced, which, upon cleavage away of the non-chymase fusion protein portion, becomes proteolytically active. A refolding procedure for increasing yields of proteolytically active recombinant chymase is provided. The invention is further directed to use of the recombinant chymase thus produced for preparing chymase-specific antibodies.

6 Claims, 8 Drawing Sheets

OTHER PUBLICATIONS

Schecter et al., 1990, "Identification of a Cathepsin G–like Proteinase in the MC$_{TC}$ Type of Human Mast Cell", J. Immunol. 145:2652–2661.

Tam and Caughey, 1990, "Degradation of Airway Neuropeptides by Human Lung Tryptase", Am. J. Respir. Cell Mol. Biol. 3:27–32.

Urata et al., 1990, "Identification of a Highly Specific Chymase as the Major Angiotensin II–forming Enzyme in the Human Heart", J. Biol. Chem. 265:22348–22357.

Birch and Loh, 1989 in "Proteolytic Enzymes: A Practical Approach" Benyon and Bonds, eds., IRL Press: Oxford, pp. 211–230.

Irani et al., 1989, "Detection of MC$_T$ and MC$_{TC}$ Types of Human Mast Cells by Immunohistochemistry Using New Monoclonal Anti–tryptase and Anti–chymase Antibodies", J. Histochem. Cytochem. 37:1509–1515.

Nettlebeck and Fink, 1989, "A Chymotrypsin–like Protease from Porcine Lung: Identification as Mast Cell Chymase by Immunolocalization and Partial Sequence Determination", Ber. Kernforschungsanlage Juelich, 17–20.

Nadel et al., 1989, "Roles of Mast Cell Proteases in Airways", Drugs 37 (Suppl. 1):51–55.

Ollerenshaw et al., 1989, "Absence of Immunocreative Vasoactive Intestinal Polypeptide in Tissue from the Lungs of Patients With Asthma", N. Eng. J. Med. 320:1244–1248.

Sommerhoff et al., 1989, "Mast Cell Chymase: A Potent Secretagogue for Airway Gland Serous Cells", J. Immunol 142:2450–2456.

Tam et al., 1989, "Protease Inhibitors Potentiate Vasoactive Intestinal Peptide (VIP)–Induced Relaxation In Isolated Human Airway", Am Rev. Respir. Dis. 139:A200.

Carrell, 1988, "Alzheimer's Disease: Enter A Protease Inhibitor", Nature 331:478–479.

Caughey et al., 1988, "Purification and Characterization of Dog Mastocytoma Chymase: Identification of an Octapeptide Conserved in Chymotryptic Leukocyte Proteinases", Biochem. Biophys. Acta. 952:142–149.

Benfey et al., 1987, "Cloning of the Mast Cell Protease, RMCP II: Evidence for Cell–Specific Expression and a Multi–Gene Family", J. Biol. Chem. 262:5377–5384.

Nagia et al., 1987, "Synthesis and Sequence–Specific Proteolysis of Hybrid Proteins Produced in Escherichia coli", Methods Enzymol. 153:461–481.

Schwartz et al., 1987, "Quantitation of Histamine, Tryptase, and Chymase in Dispersed Human T and TC Mast Cells", J. Immunol 138:2611–2615.

Irani et al., 1986, "Two Types of Human Mast Cells That Have Distinct Neutral Protease Compositions", PNAS 83:4464–4468.

Smith et al., 1984 "Human Lung Tryptase: Purification and Characterization", J. Biol. Chem. 259:11046–11051.

Schechter et al., 1983, "Human Skin Chymotrytic Proteinase. Isolation and Relation to Cathespin G and G Rat Mast Cell Proteinase I", J. Biol. Chem. 258:2973–2978.

Schwartz et al., 1981, "Tryptase from Human Pulmonary Mast Cells", J. Biol. Chem. 256:11939–11943.

Watkins, Jul. 27, 1992, "Tryptase release and clinical severity of anaesthetic reactions," Agents Actions (Special Conference Issue) C203–205.

Schwartz et al., 1987, "Tryptase levels as an indicator of mast cell activation in systemic anaphylaxis and mastocytosis," New Eng. J. Med. 316:1622–1626.

Schwartz et al., 1989, "Time course of appearance and disappearance of human mast cell tryptase in the circulation after anaphylaxi," J. Clin. Invest. 83:1551–1555.

Butrus et al., 1990, "The level of tryptase in human tears: an indicator of activation of conjunctival mast cells," Ophthalmology 97:1678–1678–1683.

Enander et al., 1991 "A new radioimmunoassay for human mast cell tryptase using monoclonal antibodies," J. Immunol. Meth. 138:39–46.

Marston, F. A. O., 1986, "The purification of eukaryotic polypeptides synthesized in Escherichia coli," Biochem. J. 240:1–12.

Pollit, S. and Zalkin, H., 1983, "Role of primary structure and disulfide bond formation in β–lactamase secretion," J. Bacteriol. 153:27–32.

Fahey, R. C. et al., 1977, "On the cysteine and cystine content of proteins: Differences between intracellular and extracellular proteins," J. Mol. Evol. 10:155–160.

FIG. 1
AMPLIFY CHYMASE cDNA BY PCR
(5' PRIMER 1 AND 3' PRIMER)
RE-AMPLIFY CHYMASE cDNA
(5' PRIMER 2 AND 3' PRIMER)
LIGATE INTO pRC/CMV
SCREEN COLONIES BY PCR
(5' PRIMER 3 AND 3' PRIMER)
LIGATE PCR PRODUCT INTO pMAL-C
EXPRESSION VECTOR

```
  1 ATC ATC GGG GGC ACA GAA TGC AAG CCA CAT TCC CGC CCC TAC ATG
    ile ile gly gly thr glu cys lys pro his ser arg pro tyr met 16 GCC TAC CTG GAA ATT GTA ACT TCC AAC GGT CCC TCA AAA TTT TGT
    ala tyr leu glu ile val thr ser asn gly pro ser lys phe cys
                                         (T)        [T]

31 GGT TTC CTT ATA AGA CGG AAC TTT GTG CTG ACG GCT CAT
    gly phe leu ile arg arg asn phe val leu thr ala his 46 TGT GCA GGA AGG TCT ATA ACA GTC ACC CTT GGA GCC CAT AAC ATA
    cys ala gly arg ser ile thr val thr leu gly ala his asn ile
                 (C)

61 ACA GAG GAA GAC ACA TGG CAG AAG CTT GAG GTT ATA AAG CAA
    thr glu glu asp thr trp gln lys leu glu val ile lys gln
             [G]

76 TTC CGT CAT CCA AAA TAT AAC ACT TCT ACT CTT CAC CAC GAT ATC
    phe arg his pro lys tyr asn thr ser thr leu his his asp ile
                     (G)

91 ATG TTA CTA AAG TTG AAG GAG AAA GCC AGC CTG ACC CTG GCT GTG
    met leu leu lys leu lys glu lys ala ser leu thr leu ala val 106 GGG ACA CTC CCC TTC CCA TCA CAA TTC AAC TTT GTC CCA CCT GGG
    gly thr leu pro phe pro ser gln phe asn phe val pro pro gly
```

FIGURE 5A

```
121  AGA ATG TGC CGG GTG GCT GGC TGG GGA AGA ACA GGT GTG TTG AAG
     arg met cys arg val ala gly trp gly arg thr gly val leu lys 136  CCG GGC TCA GAC ACT CTG CAA GAG GTG AAG CTG AGA CTC ATG GAT
     pro gly ser asp thr leu gln glu val lys leu arg leu met asp 151  CCC CAG GCC TGC AGC CAC TTC AGA GAC TTT GAC CAC AAT CTT CAG
     pro gln ala cys ser his phe arg asp phe asp his asn leu gln 166  CTG TGT GTG GGC AAT CCC AGG AAG ACA AAA TCT GCA TTT AAG GGA
     leu cys val gly asn pro arg lys thr lys ser ala phe lys gly
                                     [G]
181  GAC TCT GGG GGC CTT CTG TGT GCT GGG GTG GCC CAG GGC ATC
     asp ser gly gly leu leu cys ala gly val ala gln gly ile 196  GTA TCC TAT GGA CGG TCG GAT GCA AAG CCC CCT GCT GTC TTC ACC
     val ser tyr gly arg ser asp ala lys pro pro ala val phe thr 211  CGA ATC TCC CAT TAC CGG CCC TGG AAC CAG ATC CTG CAG GCA
     arg ile ser his tyr arg pro trp ile asn gln ile leu gln ala 226  AAT TAA
     asn ***
```

FIGURE 5B

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 681 base pairs
        ( B ) TYPE: nucleic acid
        ( C ) STRANDEDNESS: double
        ( D ) TOPOLOGY: unknown ( i i ) MOLECULE TYPE: DNA ( i x ) FEATURE:
        ( A ) NAME/KEY: CDS
        ( B ) LOCATION: 1..678

( x i ) SEQUENCE DESCRIPTION: SEQ ID NO:1:

| | | | | | | | | | | | | | | | | |
|---|---|---|---|---|---|---|---|---|---|---|---|---|---|---|---|---|
| ATC | ATC | GGG | GGC | ACA | GAA | TGC | AAG | CCA | CAT | TCC | CGC | CCC | TAC | ATG | GCC | 48 |
| Ile | Ile | Gly | Gly | Thr | Glu | Cys | Lys | Pro | His | Ser | Arg | Pro | Tyr | Met | Ala | |
| 1 | | | | 5 | | | | | 10 | | | | | 15 | | |
| TAC | CTG | GAA | ATT | GTA | ACT | TCC | AAC | GGT | CCC | TCA | AAA | TTT | TGT | GGT | GGT | 96 |
| Tyr | Leu | Glu | Ile | Val | Thr | Ser | Asn | Gly | Pro | Ser | Lys | Phe | Cys | Gly | Gly | |
| | | | 20 | | | | | 25 | | | | | 30 | | | |
| TTC | CTT | ATA | AGA | CGG | AAC | TTT | GTG | CTG | ACG | GCT | GCT | CAT | TGT | GCA | GGA | 144 |
| Phe | Leu | Ile | Arg | Arg | Asn | Phe | Val | Leu | Thr | Ala | Ala | His | Cys | Ala | Gly | |
| | | 35 | | | | | 40 | | | | | 45 | | | | |
| AGG | TCT | ATA | ACA | GTC | ACC | CTT | GGA | GCC | CAT | AAC | ATA | ACA | GAG | GAA | GAA | 192 |
| Arg | Ser | Ile | Thr | Val | Thr | Leu | Gly | Ala | His | Asn | Ile | Thr | Glu | Glu | Glu | |
| | 50 | | | | | 55 | | | | | 60 | | | | | |
| GAC | ACA | TGG | CAG | AAG | CTT | GAG | GTT | ATA | AAG | CAA | TTC | CGT | CAT | CCA | AAA | 240 |
| Asp | Thr | Trp | Gln | Lys | Leu | Glu | Val | Ile | Lys | Gln | Phe | Arg | His | Pro | Lys | |
| 65 | | | | | 70 | | | | | 75 | | | | | 80 | |
| TAT | AAC | ACT | TCT | ACT | CTT | CAC | CAC | GAT | ATC | ATG | TTA | CTA | AAG | TTG | AAG | 288 |
| Tyr | Asn | Thr | Ser | Thr | Leu | His | His | Asp | Ile | Met | Leu | Leu | Lys | Leu | Lys | |
| | | | | 85 | | | | | 90 | | | | | 95 | | |
| GAG | AAA | GCC | AGC | CTG | ACC | CTG | GCT | GTG | GGG | ACA | CTC | CCC | TTC | CCA | TCA | 336 |
| Glu | Lys | Ala | Ser | Leu | Thr | Leu | Ala | Val | Gly | Thr | Leu | Pro | Phe | Pro | Ser | |
| | | | 100 | | | | | 105 | | | | | 110 | | | |
| CAA | TTC | AAC | TTT | GTC | CCA | CCT | GGG | AGA | ATG | TGC | CGG | GTG | GCT | GGC | TGG | 384 |
| Gln | Phe | Asn | Phe | Val | Pro | Pro | Gly | Arg | Met | Cys | Arg | Val | Ala | Gly | Trp | |
| | | 115 | | | | | 120 | | | | | 125 | | | | |
| GGA | AGA | ACA | GGT | GTG | TTG | AAG | CCG | GGC | TCA | GAC | ACT | CTG | CAA | GAG | GTG | 432 |
| Gly | Arg | Thr | Gly | Val | Leu | Lys | Pro | Gly | Ser | Asp | Thr | Leu | Gln | Glu | Val | |
| | 130 | | | | | 135 | | | | | 140 | | | | | |
| AAG | CTG | AGA | CTC | ATG | GAT | CCC | CAG | GCC | TGC | AGC | CAC | TTC | AGA | GAC | TTT | 480 |
| Lys | Leu | Arg | Leu | Met | Asp | Pro | Gln | Ala | Cys | Ser | His | Phe | Arg | Asp | Phe | |
| 145 | | | | | 150 | | | | | 155 | | | | | 160 | |
| GAC | CAC | AAT | CTT | CAG | CTG | TGT | GTG | GGC | AAT | CCC | AGG | AAG | ACA | AAA | TCT | 528 |
| Asp | His | Asn | Leu | Gln | Leu | Cys | Val | Gly | Asn | Pro | Arg | Lys | Thr | Lys | Ser | |
| | | | | 165 | | | | | 170 | | | | | 175 | | |
| GCA | TTT | AAG | GGA | GAC | TCT | GGG | GGC | CCT | CTT | CTG | TGT | GCT | GGG | GTG | GCC | 576 |
| Ala | Phe | Lys | Gly | Asp | Ser | Gly | Gly | Pro | Leu | Leu | Cys | Ala | Gly | Val | Ala | |
| | | | 180 | | | | | 185 | | | | | 190 | | | |
| CAG | GGC | ATC | GTA | TCC | TAT | GGA | CGG | TCG | GAT | GCA | AAG | CCC | CCT | GCT | GTC | 624 |
| Gln | Gly | Ile | Val | Ser | Tyr | Gly | Arg | Ser | Asp | Ala | Lys | Pro | Pro | Ala | Val | |
| | | 195 | | | | | 200 | | | | | 205 | | | | |
| TTC | ACC | CGA | ATC | TCC | CAT | TAC | CGG | CCC | TGG | ATC | AAC | CAG | ATC | CTG | CAG | 672 |
| Phe | Thr | Arg | Ile | Ser | His | Tyr | Arg | Pro | Trp | Ile | Asn | Gln | Ile | Leu | Gln | |
| | 210 | | | | | 215 | | | | | 220 | | | | | |
| GCA | AAT | TAA | | | | | | | | | | | | | | 681 |
| Ala | Asn | | | | | | | | | | | | | | | |
| 225 | | | | | | | | | | | | | | | | |

( 2 ) INFORMATION FOR SEQ ID NO:2:

( i ) SEQUENCE CHARACTERISTICS:
        ( A ) LENGTH: 226 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Ile | Ile | Gly | Gly | Thr | Glu | Cys | Lys | Pro | His | Ser | Arg | Pro | Tyr | Met | Ala |
| 1 | | | | 5 | | | | | 10 | | | | | 15 | |
| Tyr | Leu | Glu | Ile | Val | Thr | Ser | Asn | Gly | Pro | Ser | Lys | Phe | Cys | Gly | Gly |
| | | | 20 | | | | | 25 | | | | | 30 | | |
| Phe | Leu | Ile | Arg | Arg | Asn | Phe | Val | Leu | Thr | Ala | Ala | His | Cys | Ala | Gly |
| | | 35 | | | | | 40 | | | | | 45 | | | |

| | | | | | | | | | | | | | | |
|---|---|---|---|---|---|---|---|---|---|---|---|---|---|---|
| Arg | Ser | Ile | Thr | Val | Thr | Leu | Gly | Ala | His | Asn | Ile | Thr | Glu | Glu | Glu |
| | 50 | | | | | 55 | | | | | 60 | | | | |
| Asp | Thr | Trp | Gln | Lys | Leu | Glu | Val | Ile | Lys | Gln | Phe | Arg | His | Pro | Lys |
| 65 | | | | | 70 | | | | | 75 | | | | | 80 |
| Tyr | Asn | Thr | Ser | Thr | Leu | His | His | Asp | Ile | Met | Leu | Leu | Lys | Leu | Lys |
| | | | | 85 | | | | | 90 | | | | | 95 | |
| Glu | Lys | Ala | Ser | Leu | Thr | Leu | Ala | Val | Gly | Thr | Leu | Pro | Phe | Pro | Ser |
| | | | | 100 | | | | | 105 | | | | | 110 | |
| Gln | Phe | Asn | Phe | Val | Pro | Pro | Gly | Arg | Met | Cys | Arg | Val | Ala | Gly | Trp |
| | | | 115 | | | | | 120 | | | | | 125 | | |
| Gly | Arg | Thr | Gly | Val | Leu | Lys | Pro | Gly | Ser | Asp | Thr | Leu | Gln | Glu | Val |
| | | 130 | | | | | 135 | | | | | 140 | | | |
| Lys | Leu | Arg | Leu | Met | Asp | Pro | Gln | Ala | Cys | Ser | His | Phe | Arg | Asp | Phe |
| 145 | | | | | 150 | | | | | 155 | | | | | 160 |
| Asp | His | Asn | Leu | Gln | Leu | Cys | Val | Gly | Asn | Pro | Arg | Lys | Thr | Lys | Ser |
| | | | | 165 | | | | | 170 | | | | | 175 | |
| Ala | Phe | Lys | Gly | Asp | Ser | Gly | Gly | Pro | Leu | Leu | Cys | Ala | Gly | Val | Ala |
| | | | 180 | | | | | 185 | | | | | 190 | | |
| Gln | Gly | Ile | Val | Ser | Tyr | Gly | Arg | Ser | Asp | Ala | Lys | Pro | Pro | Ala | Val |
| | | 195 | | | | | 200 | | | | | 205 | | | |
| Phe | Thr | Arg | Ile | Ser | His | Tyr | Arg | Pro | Trp | Ile | Asn | Gln | Ile | Leu | Gln |
| | 210 | | | | | 215 | | | | | 220 | | | | |
| Ala | Asn | | | | | | | | | | | | | | |
| 225 | | | | | | | | | | | | | | | |

( 2 ) INFORMATION FOR SEQ ID NO:3:

( i ) SEQUENCE CHARACTERISTICS:
        ( A ) LENGTH: 681 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 1..678

( x i ) SEQUENCE DESCRIPTION: SEQ ID NO:3:

| | | | | | | | | | | | | | | | |
|---|---|---|---|---|---|---|---|---|---|---|---|---|---|---|---|
| ATC | ATC | GGG | GGC | ACA | GAA | TGC | AAG | CCA | CAT | TCC | CGC | CCC | TAC | ATG | GCC | 48 |
| Ile | Ile | Gly | Gly | Thr | Glu | Cys | Lys | Pro | His | Ser | Arg | Pro | Tyr | Met | Ala | |
| 1 | | | | 5 | | | | | 10 | | | | | 15 | | |
| TAC | CTG | GAA | ATT | GTA | ACT | TCC | AAC | GGT | CCC | TCA | AAA | TTT | TGT | GGT | GGT | 96 |
| Tyr | Leu | Glu | Ile | Val | Thr | Ser | Asn | Gly | Pro | Ser | Lys | Phe | Cys | Gly | Gly | |
| | | | 20 | | | | | 25 | | | | | 30 | | | |
| TTC | CTT | ATA | AGA | CGG | AAT | TTT | GTG | CTG | ACG | GCT | GCT | CAT | TGT | GCA | GGA | 144 |
| Phe | Leu | Ile | Arg | Arg | Asn | Phe | Val | Leu | Thr | Ala | Ala | His | Cys | Ala | Gly | |
| | | 35 | | | | | 40 | | | | | 45 | | | | |
| AGG | CCT | ATA | ACA | GTC | ACC | CTT | GGA | GCC | CAT | AAC | ATA | ACA | GAG | GAA | GAA | 192 |
| Arg | Pro | Ile | Thr | Val | Thr | Leu | Gly | Ala | His | Asn | Ile | Thr | Glu | Glu | Glu | |
| | 50 | | | | | 55 | | | | | 60 | | | | | |
| GAC | ACA | TGG | CAG | AAG | CTT | GAG | GTT | ATA | AAG | CAA | TTC | CGT | CAT | CCA | AAA | 240 |
| Asp | Thr | Trp | Gln | Lys | Leu | Glu | Val | Ile | Lys | Gln | Phe | Arg | His | Pro | Lys | |
| 65 | | | | | 70 | | | | | 75 | | | | | 80 | |
| TAT | AAC | ACT | TCT | ACT | CTT | CAC | CAC | GAT | ATC | ATG | TTA | CTA | AAG | TTG | GAG | 288 |
| Tyr | Asn | Thr | Ser | Thr | Leu | His | His | Asp | Ile | Met | Leu | Leu | Lys | Leu | Glu | |
| | | | | 85 | | | | | 90 | | | | | 95 | | |
| GAG | AAA | GCC | AGC | CTG | ACC | CTG | GCT | GTG | GGG | ACA | CTC | CCC | TTC | CCA | TCA | 336 |
| Glu | Lys | Ala | Ser | Leu | Thr | Leu | Ala | Val | Gly | Thr | Leu | Pro | Phe | Pro | Ser | |

|  |  |  |  |  |  |  |  |  |  |  |  |  |  |  |  |
|---|---|---|---|---|---|---|---|---|---|---|---|---|---|---|---|
|  |  |  | 100 |  |  |  |  | 105 |  |  |  |  | 110 |  |  |
| CAA | TTC | AAC | TTT | GTC | CCA | CCT | GGG | AGA | ATG | TGC | CGG | GTG | GCT | GGC | TGG |
| Gln | Phe | Asn | Phe | Val | Pro | Pro | Gly | Arg | Met | Cys | Arg | Val | Ala | Gly | Trp |
|  |  | 115 |  |  |  |  | 120 |  |  |  |  | 125 |  |  |  |

384

GGA AGA ACA GGT GTG TTG AAG CCG GGC TCA GAC ACT CTG CAA GAG GTG      432
Gly Arg Thr Gly Val Leu Lys Pro Gly Ser Asp Thr Leu Gln Glu Val
    130             135             140

AAG CTG AGA CTC ATG GAT CCC CAG GCC TGC AGC CAC TTC AGA GAC TTT      480
Lys Leu Arg Leu Met Asp Pro Gln Ala Cys Ser His Phe Arg Asp Phe
145             150             155             160

GAC CAC AAT CTT CAG CTG TGT GTG GGC AAT CCC AGG AAG ACA AAA TCT      528
Asp His Asn Leu Gln Leu Cys Val Gly Asn Pro Arg Lys Thr Lys Ser
            165             170             175

GCA TTT AAG GGA GAC TCT GGG GGC CCT CTT CTG TGT GCT GGG GTG GCC      576
Ala Phe Lys Gly Asp Ser Gly Gly Pro Leu Leu Cys Ala Gly Val Ala
        180             185             190

CAG GGC ATC GTA TCC TAT GGA CGG TCG GAT GCA AAG CCC CCT GCT GTC      624
Gln Gly Ile Val Ser Tyr Gly Arg Ser Asp Ala Lys Pro Pro Ala Val
        195             200             205

TTC ACC CGA ATC TCC CAT TAC CGG CCC TGG ATC AAC CAG ATC CTG CAG      672
Phe Thr Arg Ile Ser His Tyr Arg Pro Trp Ile Asn Gln Ile Leu Gln
210             215             220

GCA AAT TAA                                                          681
Ala Asn
225

( 2 ) INFORMATION FOR SEQ ID NO:4:

( i ) SEQUENCE CHARACTERISTICS:
        ( A ) LENGTH: 226 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:4:

Ile Ile Gly Gly Thr Glu Cys Lys Pro His Ser Arg Pro Tyr Met Ala
1               5                   10                  15

Tyr Leu Glu Ile Val Thr Ser Asn Gly Pro Ser Lys Phe Cys Gly Gly
            20                  25                  30

Phe Leu Ile Arg Arg Asn Phe Val Leu Thr Ala Ala His Cys Ala Gly
        35                  40                  45

Arg Pro Ile Thr Val Thr Leu Gly Ala His Asn Ile Thr Glu Glu Glu
    50                  55                  60

Asp Thr Trp Gln Lys Leu Glu Val Ile Lys Gln Phe Arg His Pro Lys
65                  70                  75                  80

Tyr Asn Thr Ser Thr Leu His His Asp Ile Met Leu Leu Lys Leu Glu
                85                  90                  95

Glu Lys Ala Ser Leu Thr Leu Ala Val Gly Thr Leu Pro Phe Pro Ser
            100                 105                 110

Gln Phe Asn Phe Val Pro Pro Gly Arg Met Cys Arg Val Ala Gly Trp
        115                 120                 125

Gly Arg Thr Gly Val Leu Lys Pro Gly Ser Asp Thr Leu Gln Glu Val
    130                 135                 140

Lys Leu Arg Leu Met Asp Pro Gln Ala Cys Ser His Phe Arg Asp Phe
145                 150                 155                 160

Asp His Asn Leu Gln Leu Cys Val Gly Asn Pro Arg Lys Thr Lys Ser
                165                 170                 175

Ala Phe Lys Gly Asp Ser Gly Gly Pro Leu Leu Cys Ala Gly Val Ala

|   |   |   | 180 |   |   |   |   | 185 |   |   |   |   | 190 |   |   |
|---|---|---|---|---|---|---|---|---|---|---|---|---|---|---|---|
| Gln | Gly | Ile | Val | Ser | Tyr | Gly | Arg | Ser | Asp | Ala | Lys | Pro | Pro | Ala | Val |
|   |   | 195 |   |   |   |   |   | 200 |   |   |   | 205 |   |   |   |

| Phe | Thr | Arg | Ile | Ser | His | Tyr | Arg | Pro | Trp | Ile | Asn | Gln | Ile | Leu | Gln |
|---|---|---|---|---|---|---|---|---|---|---|---|---|---|---|---|
|   | 210 |   |   |   | 215 |   |   |   |   | 220 |   |   |   |   |   |

| Ala | Asn |
|---|---|
| 225 |   |

( 2 ) INFORMATION FOR SEQ ID NO:5:

( i ) SEQUENCE CHARACTERISTICS:
        ( A ) LENGTH: 681 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 1..678

( x i ) SEQUENCE DESCRIPTION: SEQ ID NO:5:

| ATC | ATC | GGG | GGC | ACA | GAA | TGC | AAG | CCA | CAT | TCC | CGC | CCC | TAC | ATG | GCC | 48 |
|---|---|---|---|---|---|---|---|---|---|---|---|---|---|---|---|---|
| Ile | Ile | Gly | Gly | Thr | Glu | Cys | Lys | Pro | His | Ser | Arg | Pro | Tyr | Met | Ala |   |
| 1 |   |   |   | 5 |   |   |   |   | 10 |   |   |   |   | 15 |   |   |

| TAC | CTG | GAA | ATT | GTA | ACT | TCC | AAC | GGT | CCC | TCA | AAA | TTT | TGT | GGT | GGT | 96 |
|---|---|---|---|---|---|---|---|---|---|---|---|---|---|---|---|---|
| Tyr | Leu | Glu | Ile | Val | Thr | Ser | Asn | Gly | Pro | Ser | Lys | Phe | Cys | Gly | Gly |   |
|   |   |   | 20 |   |   |   |   | 25 |   |   |   |   | 30 |   |   |   |

| TTC | CTT | ATA | AGA | CGG | AAC | TTT | GTG | TTG | ACG | GCT | GCT | CAT | TGT | GCA | GGA | 144 |
|---|---|---|---|---|---|---|---|---|---|---|---|---|---|---|---|---|
| Phe | Leu | Ile | Arg | Arg | Asn | Phe | Val | Leu | Thr | Ala | Ala | His | Cys | Ala | Gly |   |
|   |   | 35 |   |   |   |   | 40 |   |   |   |   | 45 |   |   |   |   |

| AGG | TCT | ATA | ACA | GTC | ACC | CTT | GGA | GCC | CAT | AAC | ATA | ACA | GAG | GAA | GAA | 192 |
|---|---|---|---|---|---|---|---|---|---|---|---|---|---|---|---|---|
| Arg | Ser | Ile | Thr | Val | Thr | Leu | Gly | Ala | His | Asn | Ile | Thr | Glu | Glu | Glu |   |
|   | 50 |   |   |   |   | 55 |   |   |   |   | 60 |   |   |   |   |   |

| GAC | ACA | TGG | CAG | AAG | CTT | GAG | GTT | ATA | AAG | CAA | TTC | CGT | CAT | CCA | AAG | 240 |
|---|---|---|---|---|---|---|---|---|---|---|---|---|---|---|---|---|
| Asp | Thr | Trp | Gln | Lys | Leu | Glu | Val | Ile | Lys | Gln | Phe | Arg | His | Pro | Lys |   |
| 65 |   |   |   |   | 70 |   |   |   |   | 75 |   |   |   |   | 80 |   |

| TAT | AAC | ACT | TCT | ACT | CTT | CAC | CAC | GAT | ATC | ATG | TTA | CTA | AAG | TTG | AAG | 288 |
|---|---|---|---|---|---|---|---|---|---|---|---|---|---|---|---|---|
| Tyr | Asn | Thr | Ser | Thr | Leu | His | His | Asp | Ile | Met | Leu | Leu | Lys | Leu | Lys |   |
|   |   |   |   | 85 |   |   |   |   | 90 |   |   |   |   | 95 |   |   |

| GAG | AAA | GCC | AGC | CTG | ACC | CTG | GCT | GTG | GGG | ACA | CTC | CCC | TTC | CCA | TCA | 336 |
|---|---|---|---|---|---|---|---|---|---|---|---|---|---|---|---|---|
| Glu | Lys | Ala | Ser | Leu | Thr | Leu | Ala | Val | Gly | Thr | Leu | Pro | Phe | Pro | Ser |   |
|   |   |   | 100 |   |   |   |   | 105 |   |   |   |   | 110 |   |   |   |

| CAA | TTC | AAC | TTT | GTC | CCA | CCT | GGG | AGA | ATG | TGC | CGG | GTG | GCT | GGC | TGG | 384 |
|---|---|---|---|---|---|---|---|---|---|---|---|---|---|---|---|---|
| Gln | Phe | Asn | Phe | Val | Pro | Pro | Gly | Arg | Met | Cys | Arg | Val | Ala | Gly | Trp |   |
|   |   | 115 |   |   |   |   | 120 |   |   |   |   | 125 |   |   |   |   |

| GGA | AGA | ACA | GGT | GTG | TTG | AAG | CCG | GGC | TCA | GAC | ACT | CTG | CAA | GAG | GTG | 432 |
|---|---|---|---|---|---|---|---|---|---|---|---|---|---|---|---|---|
| Gly | Arg | Thr | Gly | Val | Leu | Lys | Pro | Gly | Ser | Asp | Thr | Leu | Gln | Glu | Val |   |
|   | 130 |   |   |   |   | 135 |   |   |   |   | 140 |   |   |   |   |   |

| AAG | CTG | AGA | CTC | ATG | GAT | CCC | CAG | GCC | TGC | AGC | CAC | TTC | AGA | GAC | TTT | 480 |
|---|---|---|---|---|---|---|---|---|---|---|---|---|---|---|---|---|
| Lys | Leu | Arg | Leu | Met | Asp | Pro | Gln | Ala | Cys | Ser | His | Phe | Arg | Asp | Phe |   |
| 145 |   |   |   |   | 150 |   |   |   |   | 155 |   |   |   |   | 160 |   |

| GAC | CAC | AAT | CTT | CAG | CTG | TGT | GTG | GGC | AAT | CCC | AGG | AAG | ACA | AAA | TCT | 528 |
|---|---|---|---|---|---|---|---|---|---|---|---|---|---|---|---|---|
| Asp | His | Asn | Leu | Gln | Leu | Cys | Val | Gly | Asn | Pro | Arg | Lys | Thr | Lys | Ser |   |
|   |   |   |   | 165 |   |   |   |   | 170 |   |   |   |   | 175 |   |   |

| GCA | TTT | AAG | GGA | GAC | TCT | GGG | GGC | CCT | CTT | CTG | TGT | GCT | GGG | GTG | GCC | 576 |
|---|---|---|---|---|---|---|---|---|---|---|---|---|---|---|---|---|
| Ala | Phe | Lys | Gly | Asp | Ser | Gly | Gly | Pro | Leu | Leu | Cys | Ala | Gly | Val | Ala |   |
|   |   |   | 180 |   |   |   |   | 185 |   |   |   |   | 190 |   |   |   |

| CAG | GGC | ATC | GTA | TCC | TAT | GGA | CGG | TCG | GAT | GCA | GAG | CCC | CCT | GCT | GTC | 624 |
|---|---|---|---|---|---|---|---|---|---|---|---|---|---|---|---|---|
| Gln | Gly | Ile | Val | Ser | Tyr | Gly | Arg | Ser | Asp | Ala | Glu | Pro | Pro | Ala | Val |   |
|   |   | 195 |   |   |   |   | 200 |   |   |   |   | 205 |   |   |   |   |

| TTC | ACC | CGA | ATC | TCC | CAT | TAC | CGG | CCC | TGG | ATC | AAC | CAG | ATC | CTG | CAG | 672 |
| Phe | Thr | Arg | Ile | Ser | His | Tyr | Arg | Pro | Trp | Ile | Asn | Gln | Ile | Leu | Gln | |
| | 210 | | | | 215 | | | | | 220 | | | | | | |

GCA AAT TAA  681
Ala Asn
225

(2) INFORMATION FOR SEQ ID NO:6:

(i) SEQUENCE CHARACTERISTICS:
        (A) LENGTH: 226 amino acids
        (B) TYPE: amino acid
        (D) TOPOLOGY: unknown (ii) MOLECULE TYPE: protein (xi) SEQUENCE DESCRIPTION: SEQ ID NO:6:

Ile Ile Gly Gly Thr Glu Cys Lys Pro His Ser Arg Pro Tyr Met Ala
1               5                   10                  15

Tyr Leu Glu Ile Val Thr Ser Asn Gly Pro Ser Lys Phe Cys Gly Gly
            20                  25                  30

Phe Leu Ile Arg Arg Asn Phe Val Leu Thr Ala Ala His Cys Ala Gly
        35                  40                  45

Arg Ser Ile Thr Val Thr Leu Gly Ala His Asn Ile Thr Glu Glu Glu
    50                  55                  60

Asp Thr Trp Gln Lys Leu Glu Val Ile Lys Gln Phe Arg His Pro Lys
65                  70                  75                  80

Tyr Asn Thr Ser Thr Leu His His Asp Ile Met Leu Leu Lys Leu Lys
                85                  90                  95

Glu Lys Ala Ser Leu Thr Leu Ala Val Gly Thr Leu Pro Phe Pro Ser
            100                 105                 110

Gln Phe Asn Phe Val Pro Pro Gly Arg Met Cys Arg Val Ala Gly Trp
        115                 120                 125

Gly Arg Thr Gly Val Leu Lys Pro Gly Ser Asp Thr Leu Gln Glu Val
    130                 135                 140

Lys Leu Arg Leu Met Asp Pro Gln Ala Cys Ser His Phe Arg Asp Phe
145                 150                 155                 160

Asp His Asn Leu Gln Leu Cys Val Gly Asn Pro Arg Lys Thr Lys Ser
                165                 170                 175

Ala Phe Lys Gly Asp Ser Gly Gly Pro Leu Leu Cys Ala Gly Val Ala
            180                 185                 190

Gln Gly Ile Val Ser Tyr Gly Arg Ser Asp Ala Glu Pro Pro Ala Val
        195                 200                 205

Phe Thr Arg Ile Ser His Tyr Arg Pro Trp Ile Asn Gln Ile Leu Gln
    210                 215                 220

Ala Asn
225

(2) INFORMATION FOR SEQ ID NO:7:

(i) SEQUENCE CHARACTERISTICS:
        (A) LENGTH: 48 nucleotides
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:7:

GCTTCTGACT ACAAGGACGA CGATGACAAG ATCATCGGGG GCACAGAA    48

( 2 ) INFORMATION FOR SEQ ID NO:8:

( i ) SEQUENCE CHARACTERISTICS:
    ( A ) LENGTH: 57 nucleotides
    ( B ) TYPE: nucleic acid
    ( C ) STRANDEDNESS: single
    ( D ) TOPOLOGY: unknown ( i i ) MOLECULE TYPE: DNA ( x i ) SEQUENCE DESCRIPTION: SEQ ID NO:8:

ATGATATTCC TTACCACCCT CCCTCTCTTT TGGATAATGA TTTCAGCTTC TGACTAC    57

( 2 ) INFORMATION FOR SEQ ID NO:9:

( i ) SEQUENCE CHARACTERISTICS:
    ( A ) LENGTH: 21 nucleotides
    ( B ) TYPE: nucleic acid
    ( C ) STRANDEDNESS: single
    ( D ) TOPOLOGY: unknown ( i i ) MOLECULE TYPE: DNA ( x i ) SEQUENCE DESCRIPTION: SEQ ID NO:9:

ATCATCGGGG GCACAGAATG C    21

( 2 ) INFORMATION FOR SEQ ID NO:10:

( i ) SEQUENCE CHARACTERISTICS:
    ( A ) LENGTH: 26 nucleotides
    ( B ) TYPE: nucleic acid
    ( C ) STRANDEDNESS: single
    ( D ) TOPOLOGY: unknown ( i i ) MOLECULE TYPE: DNA ( x i ) SEQUENCE DESCRIPTION: SEQ ID NO:10:

AATCTAGATT AATTTGCCTG CAGGAT    26

RECOMBINANT PRODUCTION OF CHYMASE

1. FIELD OF THE INVENTION

The instant invention is directed to recombinant production of chymase. The invention is further directed to use of the recombinant chymase thus produced for preparing chymase-specific antibodies and testing chymase inhibitors. The recombinant proteins of the invention are a more plentiful and purer source of chymase than natural sources.

2. BACKGROUND OF THE INVENTION

Mast cells play key roles in allergic reactions and in a number of inflammatory disorders. Following activation, mast cells release a variety of cytokines as well as histamine, proteoglycans, and lipid-derived mediators (Stevens and Austen, 1989, Immunol. Today 10:381–386; Corrigan and Kay, 1991, Am. Rev. Respir. Dis. 143:1165–1168). Tryptase and chymase, serine proteases with trypsin-like and chymotrypsin-like substrate specificities respectively, represent the major protein constituents of human mast cells and are also released upon activation (Schwartz et al., 1981, J. Biol. Chem. 256:11939–43; Schwartz et al., 1987, J. Immunol. 138:2611–2615; Smith et al., 1984, J. Biol. Chem. 259:11046–51; and Schechter et al., 1983, J. Biol. Chem. 258:2973–2978). Serine proteases such as chymases and tryptases generally require post-translational removal of N-terminal amino acids (prepro sequences) to become proteolytically active (Birch and Loh, 1989, in "Proteolytic Enzymes: a practical approach," Beynon and Bond, eds., IRL Press: Oxford, pp. 211–230). Chymase is found in only a subset of human mast cells, unlike tryptase, which is found in all human mast cells (Irani et al., 1986, Proc. Natl. Acad. Sci. U.S.A. 83:4464–4468). The role of these proteases in the allergic and inflammatory responses mediated by mast cells is not well understood. However, a number of studies suggest that these enzymes may contribute to the pathophysiology of airway disease states such as asthma and cystic fibrosis (Tam and Caughey, 1990, Am. J. Respir. Cell Mol. Biol. 3:27–32; Tam et al., 1989, Am. Rev. Respir. Dis. 139:A200; Ollerenshaw et al., 1989, N. Engl. J. Med. 320:1244–1248). Chymase, for example, is an extremely potent secretagogue for airway submucosal gland cells, suggesting a potential role for this enzyme in the abnormal mucus secretion characteristic of asthma (Sommerhoff et al., 1989, J. Immunol. 142:2450–2456).

As a first step towards understanding the role of chymase in human airway disease, a reliable source of recombinant human chymase is required to facilitate structure/function and inhibitor studies of this enzyme. Genomic DNA sequences encoding human chymase have recently been cloned; the deduced placental cDNA sequence (Caughey et al., 1991, J. Biol. Chem. 266:12956–63) is identical to the cloned heart cDNA sequence (Urata et al., 1991, J. Biol. Chem. 266:17173–79). Expression of recombinant dog chymase as a fusion protein has been disclosed, although processing of the fusion protein to form mature dog chymase was not reported (Rani et al., 1992, FASEB J. 6:A1346).

Thus there is a need in the art for reliable recombinant expression of a functionally active chymase. Moreover, there is a need in the art for recombinant expression of a chymase or derivative thereof comprising a proteolytically active chymase catalytic domain.

Citation of references hereinabove shall not be construed as an admission that such is prior art to the present invention.

3. SUMMARY OF THE INVENTION

The present invention is directed to recombinant production of a functionally active chymase or a functionally active derivative (including fragment) thereof. "Functionally active" as used herein refers to the ability to exhibit one or more functional activities of a full-length wild-type chymase protein. In one embodiment, the functional activity is the ability to bind to an anti-chymase antibody. In another embodiment, the functional activity is chymase proteolytic activity. The functionally active chymase can be a fusion protein comprising a chymase catalytic domain, the catalytic domain of chymase free of any fusion protein partner, or a proteolytically active chymase fusion protein or chymase catalytic domain. In a specific embodiment, the chymase catalytic domain is full length mature chymase as found after normal post-translational processing.

In a preferred aspect, a proteolytically inactive chymase fusion protein comprising a functionally active portion of a non-chymase protein at the amino-terminus of the chymase protein is produced, which upon cleavage away of the non-chymase fusion protein portion, becomes proteolytically active. Advantageously, such a non-chymase protein can be a bacterial protein, with its encoding DNA further comprising appropriate regulatory sequences for expression in bacteria, and which confers protection from endogenous proteolysis. Further provided are fragments, derivatives and analogs of chymase that are proteolytically active. Preferably, the chymase is a human chymase.

The invention is also directed to recombinant vectors for expression of the chymase fusion proteins or proteins comprising a chymase catalytic domain, or fragments, other derivatives, or analogs thereof. The expression vectors of the invention provide for expression in prokaryotic or eukaryotic cells. Further provided are cultured prokaryotic or eukaryotic cells which contain a recombinant vector for expression of a chymase fusion protein or a protein comprising a chymase catalytic domain, or fragments, other derivatives, or analogs thereof. In a preferred embodiment, the expression vectors encode a human chymase.

The recombinant chymase fusion proteins or recombinant chymase derivatives of the invention provide a source of chymase for preparing antibodies. In a preferred embodiment the chymase fusion protein or recombinant chymase catalytic domain can be used for structural studies, e.g., X-ray crystallography or nuclear magnetic resonance spectroscopy. Structural information can be used in the rational design of chymase inhibitors.

It is a particular advantage of the present invention that a recombinant source of chymase, purified and in large amounts, preferably human chymase, is provided. Heretofore chymase could only be obtained in small quantities from natural sources.

It is another advantage of the present invention that expression of a chymase fragment comprising a proteolytically active catalytic domain of chymase is provided.

Yet another advantage of the present invention is that a recombinant source of functionally active chymase is provided. Also advantageously provided is a method for refolding a recombinant chymase fusion protein and cleaving to release the non-chymase portion, to achieve a proteolytically active form.

4. BRIEF DESCRIPTION OF THE DRAWINGS

FIG. 1. Schematic overview of chymase cDNA amplification and cloning strategy.

FIG. 2. Agarose gel analysis of the products of the first PCR reaction with 5' primer 1. Lane 1—product of PCR amplification with 5' primer 1 and 3' primer (5 µl) (see Section 6, infra); Lane 2—PCR control run in the absence of template (5 µl); Lane 3—size markers. This assay was run on a 0.9% agarose gel.

Figure 3:
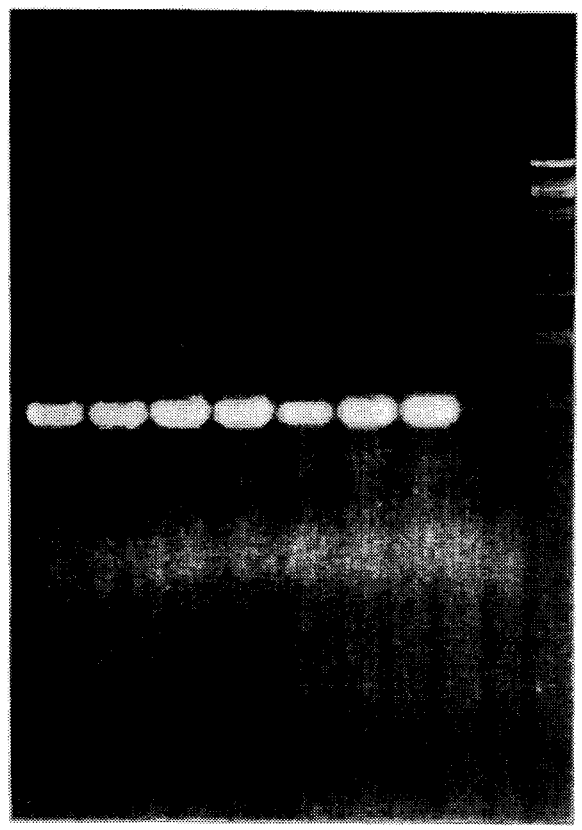

FIG. 3. Agarose gel analysis of PCR products of MBP-chymase genes cloned into *Escherichia coli*. Lanes 1–7—PCR amplified chymase genes from 7 different clones; Lane 8—control; Lane 9—size markers.

Figure 4:
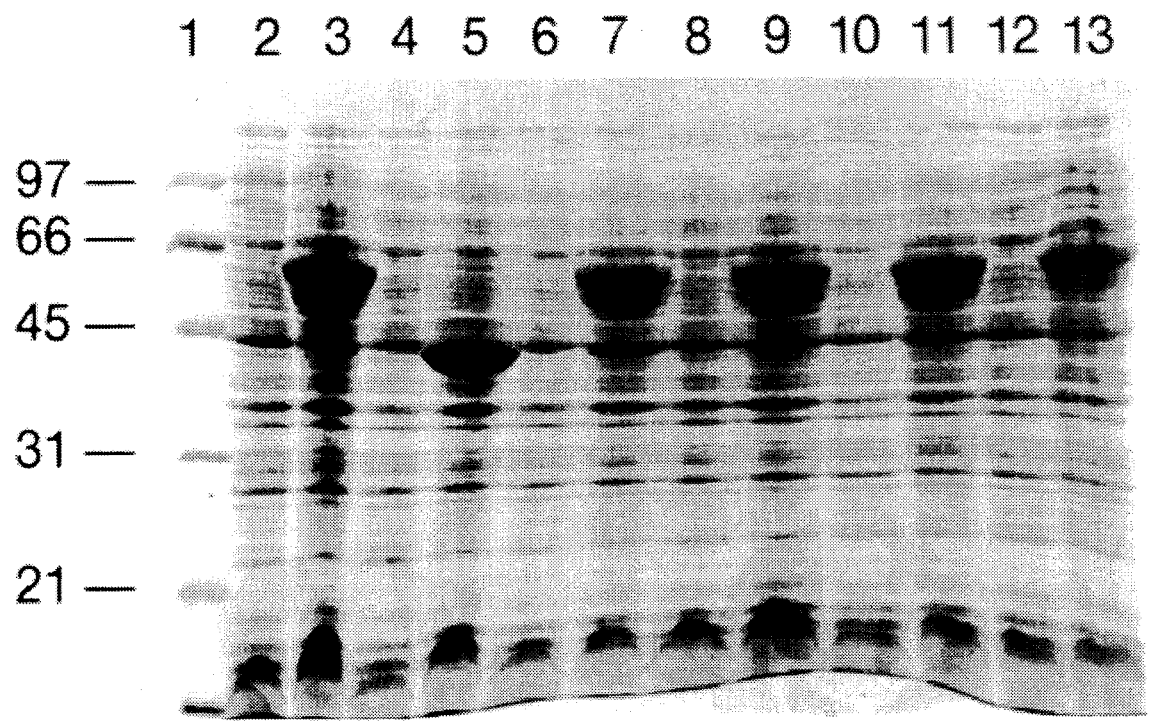

FIG. 4. Polyacrylamide gel electrophoresis analysis of proteins expressed by clones containing the recombinant MBP-chymase gene. Cells were grown and induced as described in Section 6.1.7, infra. Lane 1—molecular weight markers; Lanes 2, 4, 6, 8, 10 and 12—uninduced clones; Lanes 3, 5, 7, 9, 11 and 13—two hour, 0.1 mM IPTG induced clones. Lanes 2 and 3—clone #1; Lanes 4 and 5—clone #2; Lanes 6 and 7—clone #3; Lanes 8 and 9—clone #4; Lanes 10 and 11—clone #5; Lanes 12 and 13—clone #6.

FIG. 5. Nucleic acid and amino acid sequences of two representative human chymase cDNA clones (clones 3 and 7). The nucleic acid (SEQ ID NO:1) and amino acid (SEQ ID NO:2) sequences of wild-type human chymase (from Genbank, accession no. M64269; Caughey et al., 1991, J. Biol. Chem. 266:12956–63) are shown. The nucleotide differences of clone 7 are indicated by brackets above the wild type nucleic acid sequence. The A to G transition results in a lysine to glutamic acid change at position 204. Changes in clone 3 compared to wild type chymase are indicated by parentheses above the sequence. The A to G transition results in a lysine to glutamic acid change at position 96; the T to C transition results in a serine to proline change at position 50. One of these changes in clone 3 creates a new StuI restriction site (underlined). SEQ ID NO:3 and SEQ ID NO:4: nucleic acid and amino acid sequences, respectively, of clone 3. SEQ ID NO:5 and SEQ ID NO:6: nucleic acid and amino acid sequences, respectively, of clone 7.

Figure 6:
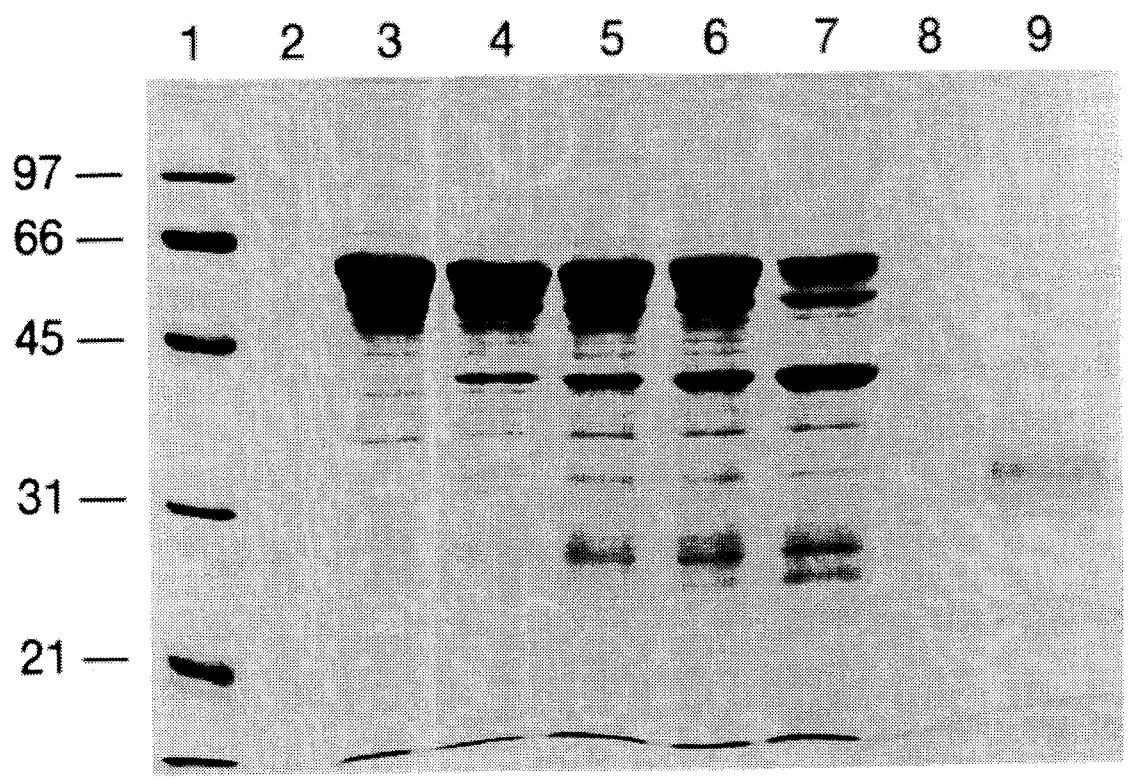

FIG. 6. Sodium dodecyl sulfate-polyacrylamide gel electrophoresis (SDS-PAGE) of Factor Xa-cleaved recombinant MBP chymase. Lane 1—molecular weight markers; Lane 2—blank; Lane 3—uncut CHYCAT/pMAL-C WT#1; Lane 4—MBP-chymase treated with Factor Xa for 1 hour; Lane 5—Factor Xa treatment for 2 hours; Lane 6—Factor Xa treatment for 4 hours; Lane 7—Factor Xa treatment for 18 hours; Lane 8—blank; Lane 9—dog chymase.

Figure 7:
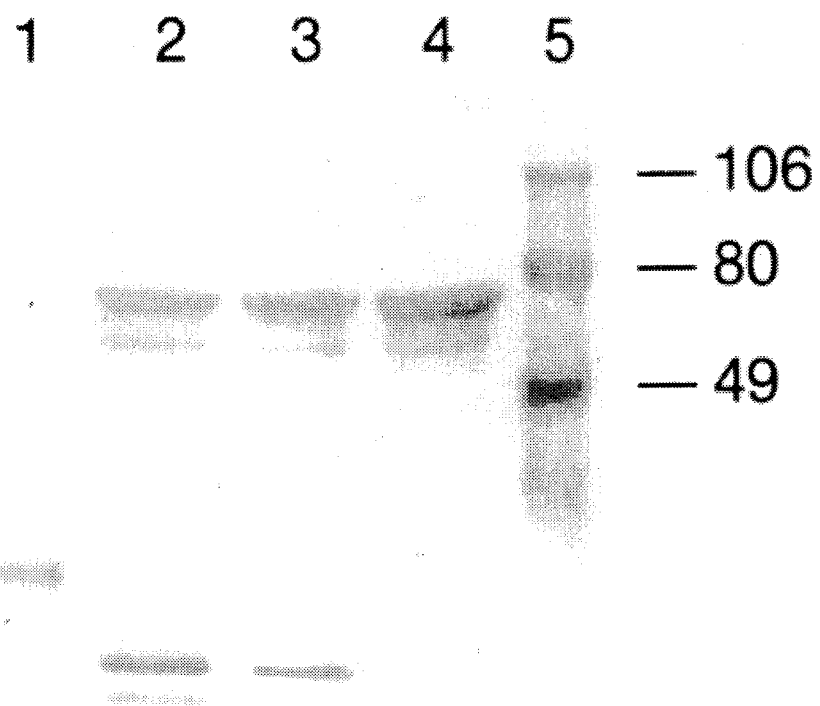

FIG. 7. Western blotting of Factor Xa-treated MBP-chymase. Chymase generated by Factor Xa cleavage was detected by a polyclonal antibody made against active dog chymase. Lane 1—dog chymase (glycosylated); Lane 2—fusion protein cleaved with Factor Xa (18 hours at room temperature); Lane 3—fusion protein cleaved with Factor Xa (18 hours at 4° C); Lane 4–intact fusion protein; Lane 5—molecular weight markers.

5. DETAILED DESCRIPTION OF THE INVENTION

The present invention is directed to recombinant production of functionally active chymase; in particular, production of a proteolytically active chymase. The invention is also directed to recombinant expression of a fusion protein comprising functionally active chymase joined via a peptide bond to a non-chymase protein or portion thereof. The invention further relates to fragments, derivatives, and analogs of chymase. In a preferred embodiment of the invention, the chymase is a human chymase.

The invention relates to production of a protein comprising a chymase catalytic domain or a chymase fusion protein comprising a chymase catalytic domain that is functionally active, i.e., capable of displaying one or more known functional activities associated with a native chymase. Such functional activities include but are not limited to antigenicity (the ability to bind—or compete with native chymase for binding—to an anti-chymase antibody), immunogenicity (ability to generate antibody which binds to chymase); and proteolytic activity (e.g., hydrolyze a chymase or chymotrypsin substrate such as the chromogenic substrate succinyl-L-PheProPhe-p-nitroanilide). In another aspect of the invention, a derivative (including fragment) or analog of chymase that is functionally active is produced.

Antibodies to chymase are also provided. Preferably such antibodies are reactive with human chymase. The antibodies of the invention can be used for the detection and quantification of chymase of human or other species. Such antibodies can also be used therapeutically, to bind chymase and neutralize its activity, e.g., by clearance through the immune system or by inhibiting the proteolytic activity of chymase.

Further provided are methods for assaying potential inhibitors of chymase to identify an inhibitor thereof. Also provided are chymase inhibitors thus identified.

By recombinant production as provided according to the present invention, enough chymase catalytic domain or chymase fusion protein is provided to allow structural studies, e.g., X-ray crystallography or nuclear magnetic resonance spectroscopy, or both. Structural studies of chymase are important for the rational design of chymase inhibitors.

As used herein, the term "recombinant chymase" refers to a chymase polypeptide expressed by a recombinant DNA molecule, preferably a recombinant DNA vector. Alternatively, the recombinant chymase can be expressed from a cloned sequence that is chromosomally integrated by recombination, e.g., homologous recombination in yeast or non-homologous recombination in mammalian cells. The recombinant chymase derivative can be a fusion protein, i.e., a chimeric protein comprising chymase and at least a functionally active portion of a non-chymase protein. The term "functionally active" as used to describe the non-chymase portion of the fusion protein refers to a portion of a non-chymase protein that is capable of (i) serving as a substrate for proteolytic cleavage (e.g., a Factor Xa sequence); (ii) binding to an antibody specific for the non-chymase protein; (iii) binding to a cognate receptor or a ligand; (iv) interacting ionically or hydrophobically with a chromatographic support; (v) catalyzing a reaction, i.e., enzymatic activity; or (vi) otherwise biologically active as assayed in vitro or in vivo. In another embodiment, the recombinant chymase derivative is a recombinant chymase fragment comprising the chymase catalytic domain expressed by a recombinant cell, or alternatively, obtained by processing of a chymase fragment fusion protein to release the non-chymase portion. In a specific embodiment, the chymase catalytic domain refers to a substantially full length amino-terminal portion of chymase protein, i.e., lacking carboxy-terminal amino acids that are not essential for catalytic activity of chymase. In a preferred embodiment, a proteolytically active recombinant chymase of the invention is a full-length chymase.

As used herein the term "proteolytically active" with reference to a chymase-related molecule refers to the ability of such molecule to mediate catalytic proteolysis of suitable substrates. Such substrates may be polypeptides, polypeptide analogs or esters, which are known substrates for serine proteases.

The present invention is based in part on the discovery that expression in a recombinant cell of a cloned chymase is unstable, normally leading to mutations such as deletions, rearrangements, and point mutations in the chymase coding sequence. While not intending to be bound by any mechanism, this instability is believed to result from selective pressure on the cell in which overexpressed proteolytically active chymase has a toxic effect due to its proteolytic activity. To avoid such instability in the cloned chymase gene, in a preferred aspect of the invention, the chymase is expressed as a fusion protein with a non-chymase portion at its amino-terminus, resulting in a fusion protein that is proteolytically inactive until cleavage away of the non-chymase portion to release a proteolytically active chymase or chymase fragment or analog. Alternatively, very tight regulation of chymase production can be employed by using an inducible promoter system, e.g., the T7 system of Studier (1990, Meth. Enzymol. 185:62–89), so as to avoid "background" levels of production of active chymase prior to induction. In addition, use of a host cell that constitutively expresses a serine protease and thus has the cellular machinery available to package expressed recombinant chymase into secretory granules may thus prevent chymase cytoxicity and nucleic acid instability.

5.1. Isolation of the Chymase Gene

The invention relates to isolated nucleic acids encoding chymase. The invention further relates to a cell line stably containing a recombinant nucleic acid encoding a chymase, and capable of expressing such nucleic acid to produce a functionally active chymase. In a preferred embodiment, the invention relates to a nucleic acid encoding human chymase. In another embodiment, the invention relates to a nucleic acid encoding primate chymase. In another embodiment, the invention relates to a nucleic acid encoding a mammalian chymase.

Derivatives of functionally active chymase, such as fragments and fusion proteins (see Section 5.6), are additionally provided, as well as nucleic acids encoding the same.

To obtain a chymase nucleic acid, in a preferred aspect, polymerase chain reaction (PCR) is used to amplify a fragment encoding a sequence comprising the chymase catalytic domain in a library, prior to selection. Oligonucleotide primers representing known chymase sequences (see, e.g., Caughey et al., 1991, J. Biol. Chem. 266:12956–63 and Urata et al., 1991, J. Biol. Chem. 266:17173–9 [human]; Caughey et al., 1990, Biochemistry 29:5166–5171 [dog]; Benfery et al., 1987, J. Biol. Chem. 262:5377 [rat chymase-like mast cell protease]) can be used as primers in PCR. Preferably such primers are prepared synthetically. The oligonucleotides may be utilized as primers to amplify by PCR sequences from a source (RNA or DNA), preferably a cDNA library, of potential interest. For example, PCR can be used to amplify a chymase coding sequence from a mast cell cDNA library, a placental cDNA library, or a skin cDNA library (mast cells in placenta and dermis make chymase). In a specific embodiment, an oligonucleotide primer pair used for PCR with a cDNA library is 5' primer 1 and 3' primer, 5' primer 2 and 3' primer, or 5' primer 3 and 3' primer, as shown in Table I, Section 6.1.2., infra. In a specific example, infra (Section 6), a set of nested 5' primers and a 3' primer are used in a two-step PCR amplification procedure. PCR can be carried out, e.g., by use of a Perkin-Elmer Cetus thermal cycler and Taq polymerase (Gene Amp™). The nucleic acid being amplified can include mRNA or cDNA from any mast cell or genomic DNA from any mammalian cell. Preferably the mRNA, cDNA or genomic DNA is from a human.

One can choose to synthesize several different degenerate primers for use in the PCR reactions. It is also possible to vary the stringency of hybridization conditions used in priming the PCR reactions, to allow for greater or lesser degrees of nucleotide sequence similarity between a chymase homolog and the known chymase. After successful amplification of a segment of a chymase homolog, that segment may be molecularly cloned and sequenced, and utilized as a probe to isolate a complete cDNA or genomic clone. This, in turn, will permit the determination of the gene's complete nucleotide sequence, the analysis of its expression, and the production of its protein product for functional analysis, as described infra. In this fashion, additional genes encoding chymase proteins may be identified and expressed.

In another embodiment, genes encoding chymase can be isolated from a suitable library by screening with a probe. Useful probes for isolating a chymase gene, preferably a human chymase gene, include dog chymase cDNA (Caughey et al., 1990, Biochemistry 29:5166–5171) or a fragment of a human chymase genomic DNA (Caughey et al., 1991, J. Biol. Chem 266:12956–12963). If a genomic library is screened, coding or non-coding fragments of the human chymase genomic cDNA can be used to select a gene encoding chymase; if a cDNA library is used, only coding fragments of the human chymase genomic DNA can be used.

A human expression library can be constructed by methods known in the art. Preferably, a cDNA library is prepared from cells or tissues that express chymase, i.e., mast cells, or from tissues that contain mast cells, such as placenta or skin. For example, human mRNA is isolated, cDNA is made and ligated into an expression vector (e.g., a bacteriophage derivative) such that it is capable of being expressed by the host cell into which it is then introduced. Various screening assays can then be used to select for the expressed human chymase product. In one embodiment, anti-chymase antibodies can be used for selection. In a preferred embodiment, the antibodies of the present invention can be used for selection. In another embodiment, proteolytic activity of the expressed chymase protein is used for selection.

The above-methods are not meant to limit the following general description of methods by which clones of chymase may be obtained.

Any mammalian cell potentially can serve as the nucleic acid source for the molecular cloning of chymase. The nucleic acid sequences encoding chymase can be isolated from human, porcine, bovine, feline, equine, as well as additional primate sources, etc. The DNA may be obtained by standard procedures known in the art from cloned DNA (e.g., a DNA "library"), by chemical synthesis, by cDNA cloning, or by the cloning of genomic DNA, or fragments thereof, purified from the desired cell (See, for example, Sambrook et al., 1989, Molecular Cloning, A Laboratory Manual, 2d Ed., Cold Spring Harbor Laboratory Press, Cold Spring Harbor, N.Y.; Glover, D.M. (ed.), 1985, DNA Cloning: A Practical Approach, MRL Press, Ltd., Oxford, U.K. Vol. I, II). Clones derived from genomic DNA may contain regulatory and intron DNA regions in addition to coding regions; clones derived from cDNA will not contain intron sequences. Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired chymase gene may be accomplished in a number of ways. For example, if an amount of a portion of a chymase gene or its specific RNA, or a fragment thereof, is available and can be purified and labeled, the generated DNA fragments may be screened by nucleic acid hybridization to the labeled probe (Benton, W. and Davis, R., 1977, Science 196:180; Grunstein, M. And Hogness, D., 1975, Proc. Natl. Acad. Sci. U.S.A. 72:3961). Those DNA fragments with substantial homology to the probe will hybridize. It is also possible to identify the appropriate fragment by restriction enzyme digestion(s) and comparison of fragment sizes with those expected according to a known restriction map if such is available. Further selection can be carried out on the basis of the properties of the gene.

Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, proteolytic activity, or antigenic properties as known for chymase. For example, dog chymase can be detected by an antibody to dog chymase (Caughey et al. 1988, Biochem. Biophys. Acta. 952:142–149). As shown in a specific example, infra, this antibody can be used to detect human recombinant chymase. In another embodiment, an antibody of the invention can be used to select for a recombinant human chymase.

It should be noted that not every expression library can be used, due to the sometimes unstable nature of recombinant chymase DNA constructs. The chymase coding sequence may destabilize a cloning vector, precluding propagation of the cloning vector in a cell. In a preferred aspect of the invention, a nucleic acid comprising a sequence encoding chymase is amplified and selected by PCR.

A chymase gene can also be identified by mRNA selection, i.e., by nucleic acid hybridization followed by in vitro translation. In this procedure, fragments are used to isolate complementary mRNAs by hybridization. Such DNA fragments may represent available, purified chymase DNA of another species (e.g., canine). Immunoprecipitation analysis or functional assays (e.g., proteolytic activity) of the in vitro translation products of the isolated products of the isolated mRNAs identifies the mRNA and, therefore, the complementary DNA fragments that contain the desired sequences. In addition, specific mRNAs may be selected by adsorption of polysomes isolated from cells to immobilized antibodies specifically directed against chymase protein. A radiolabelled chymase cDNA can be synthesized using the selected mRNA (from the adsorbed polysomes) as a template. The radiolabelled mRNA or cDNA may then be used as a probe to identify the chymase DNA fragments from among other genomic DNA fragments.

Alternatives to isolating the chymase genomic DNA or cDNA include, but are not limited to, chemically synthesizing the gene sequence itself from a known sequence or making cDNA to the mRNA which encodes the chymase protein. For example, RNA for cDNA cloning of the chymase gene can be isolated from cells which express chymase, such as mast cells. Other methods are possible and within the scope of the invention.

The identified and isolated gene can then be inserted into an appropriate cloning vector. However, a cloning vector containing a chymase coding sequence may be unstable. Cloning vectors per se are stable; they can become unstable when a chymase cDNA vector is cloned into the vector without engineering the vector to avoid instability. Avoiding instability depends on understanding the cause. It is believed that in the case of chymase, instability is due to expression of a protein product that is toxic to the host cell. Toxicity imposes a selective pressure to eliminate expression of the toxic protein; thus cells will mutate the cloned gene via deletion, insertion, point mutation, etc., while retaining parts of the plasmid required for viability (an origin of replication and an antibiotic resistance gene, for example). Solutions to the problem of instability include choosing a vector in which transcription of the cloned chymase cDNA is effectively completely repressed (not "leaky"), i.e., the level of expression is so low that there is no detectable expressed protein, until induction is desired (e.g., Studier, 1990, Meth. Enzymol. 185:62–82); expressing an enzymatically inactive form of the protein, e.g., a fusion protein; choosing a host that tolerates expression better, including a yeast or mammalian host, or using a baculovirus vector for expression in insect cells.

In addition, instability can be combatted by selecting a host to propagate the cloning vector that has been modified to eliminate some of the enzymatic pathways that mediate deletions, e.g., by using a mutant *Escherichia coli,* such as SURE cells (Stratagene, San Diego, Calif.).

With these parameters in mind, a large number of vector-host systems known in the art may be used. Possible vectors include, but are not limited to, plasmids or modified viruses, but the vector system must be compatible with the host cell used. In a preferred aspect of the invention, the chymase coding sequence is inserted in a fusion protein expression vector. The fusion protein stabilizes the vector. In another embodiment, a host cell is selected that stably expresses a serine protease constitutively, thus providing a stable environment for the vector. Such vectors include, but are not limited to, bacteriophages such as lambda derivatives, or plasmids such as PBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and chymase gene may be modified by homopolymeric tailing. Recombinant molecules can be introduced into host cells via transformation, transfection, infection, electroporation, etc., so that many copies of the gene sequence are generated.

In an alternative method, the desired gene may be identified and isolated after insertion into a suitable cloning vector in a "shot gun" approach. Enrichment for the desired gene, for example, by size fractionation, can be done before insertion into the cloning vector.

In specific embodiments, transformation of host cells with recombinant DNA molecules that incorporate the isolated chymase gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

5.2. Expression of the Chymase Gene

The nucleotide sequence coding for a chymase protein or a functionally active fragment or other derivative thereof (see Section 5.6), can be inserted into an appropriate expression vector, i.e., a vector which contains the necessary elements for the transcription and translation of the inserted protein-coding sequence. An expression vector also preferably includes a replication origin. The necessary transcriptional and translational signals can also be supplied by the native chymase gene and/or its flanking regions. In a specific embodiment, the promoter is not a chymase gene promoter. A variety of host-vector systems may be utilized to express the protein-coding sequence, as long as the chymase gene is stable in the host-vector system. Stability may be assessed by purifying the expression vector from the host-vector system and confirming structural integrity of the chymase gene (e.g., by restriction enzyme digestion, etc.). Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

In an alternative embodiment, a recombinant chymase or chymase derivative is expressed chromosomally, after integration of the chymase coding sequence by recombination.

In a specific embodiment, a chymase fusion protein can be expressed. A chymase fusion protein comprises at least a functionally active portion of a non-chymase protein joined via a peptide bond to at least a functionally active portion of a chymase protein. The non-chymase sequences can be amino- or carboxy-terminal to the chymase sequences. More preferably, for stable expression of a proteolytically inactive chymase fusion protein, the portion of the non-chymase fusion protein is joined via a peptide bond to the amino terminus of the chymase protein. A recombinant DNA molecule encoding such a fusion protein comprises a sequence encoding at least a functionally active portion of a non-chymase protein joined in-frame to the chymase coding sequence, and preferably encodes a cleavage site for a specific protease, e.g., Factor Xa, preferably at the chymase-non-chymase juncture. Expression of such a fusion protein is preferred to avoid the unstable expression of chymase. Although the present invention is not to be limited by any particular theory, it is believed that expression of a proteolytically active chymase or chymase derivative can be detrimental to the host cell. Thus, expression of a fusion protein comprising a chymase catalytic domain that lacks catalytic activity while fused to a non-chymase portion avoids this detrimental effect. In a preferred aspect, cleavage to remove the non-chymase portion of the expressed protein results in a proteolytically active chymase protein or derivative. In a preferred embodiment, the fusion protein is expressed in *Escherichia coli*.

In another specific embodiment, a fragment of chymase comprising the catalytic domain of the chymase gene is expressed as a free (non-fusion) protein. Preferably, the fragment is expressed in a cell that constitutively expresses a protease, more preferably a serine protease. In a preferred embodiment, a human cell line that constitutively expresses tryptase can be used. In another embodiment, an expression system in a cell such as *Escherichia coli* is prepared such that expression is under tight control, e.g., by use of an inducible, tightly regulated (non-leaky) promoter. In the absence of expression, the recombinant cell is stable; thus, the cell can be propagated until expression is desired.

In another embodiment, a periplasmic form of the fusion protein (containing a signal sequence) can be produced for export of the protein to the *Escherichia coli* periplasm. Export to the periplasm can promote proper folding of the expressed protein. Enzymatically active chymase can be recovered from the periplasm after Factor Xa cleavage (without going through a refolding procedure).

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination). Expression of nucleic acid sequence encoding a chymase protein or peptide fragment may be regulated by a second nucleic acid sequence so that the chymase protein or peptide is expressed in a host transformed with the recombinant DNA molecule. For example, expression of a chymase protein may be controlled by any promoter/enhancer element known in the art, but these regulatory elements must be functional in the host selected for expression. Promoters which may be used to control chymase gene expression include, but are not limited to, the SV40 early promoter region (Benoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; plant expression vectors comprising the nopaline synthetase promoter region (Herrera-Estrella et al., Nature 303:209–213) or the cauliflower mosaic virus 35S RNA promoter (Gardner, et al., 1981, Nucl. Acids Res. 9:2871), and the promoter of the photosynthetic enzyme ribulose biphosphate carboxylase (Herrera-Estrella et al., 1984, Nature 310:115–120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58), alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94), myelin basic protein gene control region which is active in oligodendrocyte cells in the brain (Readhead et al., 1987, Cell 48:703–712), myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

In a preferred embodiment, chymase is expressed in a baculovirus expression system (see, e.g., Bishop, 1990, Curr. Op. Biotechnology 1:62–67). In one embodiment, the chymase is expressed in a baculovirus expression system as a fusion protein, e.g., the MBP-chymase fusion protein described in Section 6, infra, can be expressed. In a preferred embodiment, a linearized baculovirus DNA is recombined with the nucleic acid encoding the chymase, in order to enhance the recovery of recombinant virus expression vectors (Kitts et al., 1990, Nucl. Acids Res. 18:5667–5672). In a more preferred embodiment, the linearized baculovirus DNA contains a lethal deletion that is complemented by co-transfection with an appropriate transfer vector comprising the nucleic acid encoding chymase and the gene required to complement the lethal deletion (e.g., as provided by PharMingen, San Diego, California).

Expression vectors containing chymase gene inserts can be identified by four general approaches: (a) PCR amplification of the desired plasmid DNA or specific mRNA, (b) nucleic acid hybridization, (c) presence or absence of "marker" gene functions, and (d) expression of inserted sequences. In the first approach, the nucleic acids can be amplified by PCR with incorporation of radionucleotides or stained with ethidium bromide to provide for detection of the amplified product. In the second approach, the presence of a foreign gene inserted in an expression vector can be detected by nucleic acid hybridization using probes comprising sequences that are homologous to an inserted chymase gene. In the third approach, the recombinant vector/host system can be identified and selected based upon the presence or absence of certain "marker" gene functions (e.g., β-galactosidase activity, thymidine kinase activity, resistance to antibiotics, transformation phenotype, occlusion body formation in baculovirus, etc.) caused by the insertion of foreign genes in the vector. In a specific example, the fusion protein comprises the "marker" gene product and chymase. In another example, if the chymase gene is inserted within the marker gene sequence of the vector, recombinants containing the chymase insert can be identified by the absence of the marker gene function. In the fourth approach, recombinant expression vectors can be identified by assaying for the activity of the chymase gene product expressed by the recombinant. Such assays can be based, for example, on the physical or functional properties of the chymase gene product in vitro assay systems, e.g., proteolytic activity or binding with antibody.

Preferably if a fusion protein vector is used, the DNA sequence encoding the fusion protein is engineered to encode a cleavage site in the protein for cleavage of the chymase from the fusion protein partner. In a preferred embodiment, the cleavage site is a substrate for a proteolytic enzyme. In a specific example, the cleavage site is the substrate for Factor Xa. In other embodiments, the cleavage site can be the substrate for other proteases including but not limited to collagenase, enterokinase, thrombin, and trypsin. However, in an embodiment in which the amino-terminus of chymase is fused to a non-chymase sequence and one desires to release a proteolytically active chymase, care should be taken to use a protease that gives high specificity of cleavage, so as to generate a chymase with an intact amino-terminus. Proteases such as Factor Xa, which displays high specificity, are thus preferred. The amino acid sequence of a Factor Xa cleavage site is Ile-Glu-Gly-Arg. In another embodiment, the cleavage site is sensitive to chemical cleavage. For example, if the cleavage site contains methionine, cyanogen bromide can be used to cleave the chymase from the fusion protein partner. In such an embodiment, preferably some or all of the codons for methionine in the chymase gene are mutated to express a different, non-cyanogen bromide-sensitive, amino acid with similar properties to methionine, e.g., valine, to preclude undesired cleavage of the chymase protein.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered chymase protein may be controlled. Furthermore, different host cells have characteristic and specific mechanisms for the translational and post-translational processing and modification (e.g., glycosylation, cleavage [e.g., of signal sequence]) of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of a heterologous mammalian chymase protein. Furthermore, different vector/host expression systems may effect processing reactions, such as proteolytic cleavages, to a different extent. It is interesting to note that, as shown in the examples, infra, glycosylation is not essential for enzymatic activity, since the bacterial-produced chymase (i.e., lacking carbohydrates) was enzymatically active.

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990).

Both cDNA and genomic sequences can be cloned and expressed.

5.3. Identification and Purification of the Expressed Gene Product

Once a recombinant which expresses the chymase gene sequence is identified, the recombinant chymase product can be analyzed. This is achieved by assays based on the physical or functional properties of the product, including radioactive labelling of the product followed by analysis by gel electrophoresis, immunoassay, etc.

Once the recombinant chymase protein is identified, it may be isolated and purified by standard methods including chromatography (e.g., ion exchange, affinity, and sizing column chromatography), centrifugation, differential solubility, or by any other standard technique for the purification of proteins. In a specific embodiment, the protein is purified on a MonoQ FPLC anion exchange column, or similar high performance anion exchanger. In another embodiment, the recombinant chymase is purified by immunoaffinity chromatography with an anti-chymase antibody. In a preferred embodiment, the antibody is a rat antibody. In a more preferred embodiment, the antibody is a rat monoclonal antibody. The functional properties may be evaluated using any suitable assay (see Section 5.7).

In another embodiment, in which recombinant chymase is expressed as a fusion protein, the non-chymase portion of the fusion protein can be targeted for affinity purification. For example, antibody specific for the non-chymase portion of the fusion protein can be immobilized on a solid support, e.g., cyanogen bromide-activated Sepharose, and used to purify the fusion protein. In another embodiment, a binding partner of the non-chymase portion of the fusion protein, such as a receptor or ligand, can be immobilized and used to affinity purify the fusion protein. In a specific embodiment described in an Example, infra, the non-chymase portion of the fusion protein is maltose binding protein (MBP), and amylose (a ligand of MBP) affinity resin is used to purify the fusion protein.

In a most preferred aspect, the chymase fusion protein is purified by MonoQ FPLC anion exchange chromatography.

In one embodiment, a chymase fusion protein, preferably purified, is used without further modification, i.e., without cleaving or otherwise removing the non-chymase portion of the fusion protein. In a preferred embodiment, the chymase fusion protein can be used as an immunogen to generate chymase-specific or chymase-fusion-protein-specific antibodies. In a specific embodiment, the purified chymase fusion protein can be used to immunize a rat to generate chymase specific antisera, polyclonal antibodies, and monoclonal antibodies. In a more preferred aspect, polyclonal antibodies are produced in a rabbit.

In a further embodiment, the purified fusion protein is treated to cleave the non-chymase protein or portion thereof from chymase. For example, where the fusion protein has been prepared to include a protease sensitive cleavage site, the fusion protein can be treated with the protease to cleave the protease specific site and release chymase. In a specific embodiment, the fusion protein is cleaved by treatment with Factor Xa. Cleavage of an amino-terminal non-chymase protein is particularly preferred to yield a proteolytically active chymase.

In a preferred aspect, the fusion protein can be refolded prior to or after cleavage to form a proteolytically active chymase. Preferably, refolding is done before cleavage of the non-chymase portion of the fusion protein joined to the amino-terminus of chymase to yield a properly folded, but proteolytically inactive chymase fusion protein. Factor Xa cleavage can proceed more efficiently on the refolded protein, since the non-refolded fusion protein can potentially aggregate.

The present invention is based in part upon the discovery of a suitable refolding procedure for chymase and its derivatives. In a preferred aspect of the invention, the chymase protein is refolded by the steps of (i) incubating the chymase protein in a denaturing buffer that contains a reducing agent, and then (ii) incubating the protein in a buffer that contains an oxidizing agent, and preferably also contains a protein stabilizing agent or a chaotropic agent, or both. Suitable redox (reducing/oxidizing) agent pairs include, but are not limited to, reduced glutathione/glutathione disulfide, cystine/cysteine, cystamine/cysteamine, and 2-mercaptoethanol/2-hydroxyethyldisulfide. In a preferred embodiment, the fusion protein is solubilized in a denaturant, such as urea, prior to exchange into the reducing buffer. In a more preferred embodiment, the protein is also purified, e.g., by ion exchange chromatography, prior to exchange into the reducing buffer. The denatured fusion protein is exchanged into a reducing buffer that contains a reducing agent as described above, and a denaturing agent. Denaturing agents include but are not limited to urea and, more preferably, guanidine-HCl. In a specific embodiment, the reducing buffer comprises 0.1M Tris-HCl, pH 8.7, 1 mM EDTA, 6M guanidine-HCl, 0.15M NaCl, and 0.3 mM reduced glutathione. The fusion protein is incubated in the reducing buffer for about 1 to about 24 hours, preferably about 2 to about 16 hours, at room temperature.

Preferably the fusion protein is then diluted about at least 10-fold, more preferably about 100-fold, into an oxidizing buffer that contains an oxidizing agent, such as but not limited to 0.1M Tris-HCl, pH 8.0, 1 mM EDTA, 0.15M NaCl, 0.3M oxidized glutathione. The fusion protein is then incubated for about 1 to about 24 hours, preferably about 2 to about 16 hours, at room temperature in the oxidizing buffer. In a preferred embodiment, the oxidizing buffer comprises a protein stabilizing agent, e.g., a sugar, an alcohol, or ammonium sulfate. In a specific embodiment, the protein stabilizing agent is ammonium sulfate at 1M. In another preferred embodiment, the second redox buffer comprises a chaotropic agent at low concentration, to destabilize incorrect intermolecular interactions and thus promote proper folding. Suitable chaotropic agents include but are not limited to a detergent, a polyol, L-arginine, guanidine-HCl and polyethylene glycol (PEG). It is important to use a low enough concentration of the chaotropic agent to avoid denaturing the protein. In a specific embodiment, the chaotropic agent is PEG-3400, e.g., at about 3 mg/ml. In another specific embodiment, the chaotropic agent is the detergent lauryl maltoside, e.g., at about 3 mg/ml. Then the refolded fusion protein is concentrated by at least about 10-fold, more preferably by the amount it was diluted into the oxidizing buffer. After refolding, the fusion protein can be treated to cleave the fusion protein partner and release the proteolytically active chymase portion of the protein. In a specific embodiment, the fusion protein is cleaved with Factor Xa. In a preferred embodiment, the yield of proteolytically active chymase is greater than about 1%. More preferably, the yield of proteolytically active chymase is about 40%, most preferably about 60%. Yields of greater than about 60% are also contemplated by the invention.

In a specific embodiment of the present invention, such recombinant chymase proteins include but are not limited to those containing, as a primary amino acid sequence, all or part of the amino acid sequence substantially as depicted in FIG. 5, as well as fragments and other derivatives, and analogs thereof.

5.4. Structure of the Chymase Protein

The structure of the recombinant chymase protein can be analyzed by various methods known in the art. Preferably, the structure of the chymase catalytic domain is analyzed. In one embodiment, the structure of the unglycosylated chymase catalytic domain, e.g., expressed under conditions that preclude glycosylation, for example, in bacteria, is studied. In another embodiment, the structure of the glycosylated chymase catalytic domain is studied. A glycosylated chymase catalytic domain can be obtained by expression in yeast, or more preferably, in mammalian cells, as described in Section 5.2, supra. An advantage of analyzing the structure of the glycosylated chymase catalytic domain is that this structure is expected to correspond more exactly to the structure of native chymase. Once the structure of chymase is determined, rational design of chymase inhibitors can proceed more exactly. In a specific embodiment, the amino acid sequence of a human chymase protein comprises the sequence substantially as depicted in FIG. 5, and detailed in Section 6, infra.

The chymase protein sequence can be further characterized by a hydrophilicity analysis (Hopp, T. and Woods, K., 1981, Proc. Natl. Acad. Sci. U.S.A. 78:3824). A hydrophilicity profile can be used to identify the hydrophobic and hydrophilic regions of the chymase protein. Hydrophilic regions are more likely to be immunogenic.

Secondary, structural analysis (Chou, P. and Fasman, G., 1974, Biochemistry 13:222) can also be done, to identify regions of chymase that assume specific secondary structures.

Manipulation, translation, and secondary structure prediction, as well as open reading frame prediction and plotting, can also be accomplished using computer software programs available in the art.

By providing an abundant source of recombinant chymase, the present invention enables quantitative structural determination of chymase. In particular, enough material is provided for nuclear magnetic resonance (NMR), infrared (IR), Raman, and ultraviolet (UV), especially circular dichroism (CD), spectroscopic analysis. In particular NMR provides very powerful structural analysis of molecules in solution, which more closely approximates their native environment (Marion et al., 1983, Biochem. Biophys. Res. Comm. 113:967–974; Bar et al., 1985, J. Magn. Reson. 65:355–360; Kimura et al., 1980, Proc. Natl. Acad. Sci. U.S.A. 77:1681–1685). Other methods of structural analysis can also be employed. These include but are not limited to X-ray crystallography (Engstom, A., 1974, Biochem. Exp. Biol. 11:7–13). More preferably, co-crystals of chymase and a chymase specific substrate can be studied. Analysis of co-crystals provides detailed information about inhibitor binding. Computer modeling can also be used, especially in connection with NMR or X-ray methods (Fletterick, R. and Zoller, M. (eds.), 1986, Computer Graphics and Molecular Modeling, in Current Communications in Molecular Biology, Cold Spring Harbor Laboratory, Cold Spring Harbor, N.Y.).

5.5. Generation of Antibodies to Chymase Proteins and Derivatives Thereof

According to the invention, recombinant chymase, its fragments or other derivatives, or analogs thereof, or cells expressing the foregoing may be used as an immunogen to generate antibodies which recognize chymase, preferably human chymase. Such antibodies include but are not limited to polyclonal, monoclonal, chimeric, single chain, Fab fragments, and an Fab expression library. Preferably, such antibodies are not reactive with tryptase.

Various procedures known in the art may be used for the production of polyclonal antibodies to a recombinant chymase or derivative or analog thereof. For the production of antibody, various host animals can be immunized by injection with the recombinant chymase protein, or a derivative (e.g., fragment) thereof, including but not limited to rabbits, mice, rats, etc. In one embodiment, the recombinant chymase or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and Corynebacterium parrum.

In a particular embodiment, rat polyclonal antibodies to an epitope of chymase encoded by a sequence depicted in FIG. 5, or a subsequence thereof, can be obtained. Preferably such antibodies are specifically reactive with denatured human chymase (and can thus be used, for example, in a western blot procedure); in a preferred aspect, such an antibody is not reactive with chymase proteins of other species.

For preparation of monoclonal antibodies directed toward a chymase or analog thereof, any technique which provides for the production of antibody molecules by continuous cell lines in culture may be used. These include but are not limited to the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026–2030) or by transforming human B cells with EBV virus in vitro (Cole et al., 1985, in Monoclonal Antibodies and Cancer Therapy, Alan R. Liss, pp. 77–96). In fact, according to the invention, techniques developed for the production of "chimeric antibodies" (Morrison et al., 1984, Proc. Natl. Acad. Sci. U.S.A. 81:6851–6855; Neuberger et al., 1984, Nature 312:604–608; Takeda et al., 1985, Nature 314:452–454) by splicing the genes from a mouse antibody molecule specific for chymase together with genes from a human antibody molecule of appropriate biological activity can be used; such antibodies are within the scope of this invention.

In a specific embodiment, the invention provides rat monoclonal antibodies specific for chymase. By way of example but not limitation, the following procedure is used: Two male Lewis rats are immunized intraperitoneally (i.p.) with 50–100 μg of recombinant chymase in Freund's Complete Adjuvant. On day 14, they are boosted with 50–100 μg i.p. in Incomplete Freund's Adjuvant. A test bleed is obtained at day 24 to determine antibody characteristics and relative titers. I.P. immunizations are repeated in Incomplete Freund's Adjuvant until antibody titers are sufficient to warrant a fusion. Four days prior to the fusion day, the animal is given a final i.p. boost of 50–100 μg of recombinant chymase in Incomplete Freund's Adjuvant. On fusion day, the rat is bled (providing polyclonal antibodies in the antiserum) and sacrificed, and the spleen removed. Splenocytes are combined 1:1 with the murine myeloma fusion partner P3X8.653 in the presence of PEG (MW 1200–1600). Hybrids are selected with HAT medium. No feeder cells are used. Supernatants from hybrid wells are tested for antibody titers and characteristics 10–13 days after fusion. Positive hybrids are expanded and frozen in liquid nitrogen. Antibody screens can be any of the screens described infra, including but not limited to indirect ELISA, immunoprecipitation, neutralization of enzymatic activity, etc. Selected hybrids are cloned by limiting dilution and purified antibody is prepared from serum free medium or ascites production. Preferably, such monoclonal antibodies are specific for human chymase.

According to the invention, techniques described for the production of single chain antibodies (U.S. Pat. No. 4,946,778) can be adapted to produce chymase-specific single chain antibodies. An additional embodiment of the invention utilizes the techniques described for the construction of Fab expression libraries (Huse et al., 1989, Science 246:1275–1281) to allow rapid and easy identification of monoclonal Fab fragments with the desired specificity for chymase or its derivatives, or analogs.

Antibody fragments which contain the idiotype of the antibody molecule can be generated by known techniques. For example, such fragments include but are not limited to: the F(ab')2 fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of a chymase, one may assay generated hybridomas for a product which binds to a chymase fragment containing such epitope. For selection of an antibody specific to human chymase, one can select on the basis of positive binding to human chymase and a lack of binding to chymase from another species, e.g., murine or canine chymase.

The foregoing antibodies can be used in methods known in the art relating to the localization and activity of chymase or the recombinant chymase of the invention (see Section 5.7, infra), e.g., for Western blotting, imaging chymase, measuring levels thereof in appropriate physiological samples, etc.

5.6. Chymase Derivatives and Analogs

The invention further relates to derivatives (including but not limited to fragments) and analogs of chymase. Preferably, a catalytically active chymase fragment is provided. An antigenic fragment can be any portion of chymase sufficient for immunospecific binding, e.g., about six or more amino acids.

The production and use of derivatives and analogs related to chymase are within the scope of the present invention. In a specific embodiment, the derivative or analog is functionally active, i.e., capable of exhibiting one or more functional activities associated with a full-length, wild-type chymase protein. As one example, such derivatives or analogs which have the desired immunogenicity or antigenicity can be used, for example, in immunoassays, or for immunization for inhibition of chymase activity, etc. Derivatives or analogs of chymase can be tested for the desired activity by procedures known in the art, including but not limited to the assays described in Section 5.7.

In particular, chymase derivatives can be made by altering chymase encoding nucleic acid sequences by substitutions, additions or deletions that provide for functionally equivalent molecules. Due to the degeneracy of nucleotide coding sequences, other DNA sequences which encode substantially the same amino acid sequence as a chymase gene may be used in the practice of the present invention. These include but are not limited to nucleotide sequences comprising all or portions of chymase genes which are altered by the substitution of different codons that encode the same amino acid residue within the sequence, thus producing a silent change. Likewise, the chymase derivatives of the invention include, but are not limited to, those containing, as a primary amino acid sequence, all or part of the amino acid sequence of a chymase protein including altered sequences in which functionally equivalent amino acid residues are substituted for residues within the sequence resulting in a conservative amino acid substitution. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

Derivatives or analogs of chymase include but are not limited to those peptides which are substantially homologous to chymase or fragments thereof, or whose encoding nucleic acid is capable of hybridizing to a chymase nucleic acid.

The chymase derivatives and analogs of the invention can be produced by various methods known in the art. The manipulations which result in their production can occur at the gene or protein level. For example, the cloned chymase gene sequence can be modified by any of numerous strategies known in the art (Maniatis, T., 1990, Molecular Cloning, A Laboratory Manual, 2d ed., Cold Spring Harbor Laboratory, Cold Spring Harbor, New York). The sequence can be cleaved at appropriate sites with restriction endonuclease(s), followed by further enzymatic modification if desired, isolated, and ligated in vitro. In the production of the gene encoding a derivative or analog of chymase, care should be taken to ensure that the modified gene remains within the same translational reading frame as chymase, uninterrupted by translational stop signals, in the gene region where the desired chymase activity is encoded.

Additionally, the chymase-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479–488; Oliphant et al., 1986, Gene 44:177; Hutchinson et al., 1986, Proc. Natl. Acad. Sci. U.S.A. 83:710), use of TAB® linkers (Pharmacia), etc. PCR techniques are preferred for site directed mutagenesis (see Higuchi, 1989, "Using PCR to Engineer DNA" in , PCR Technology: Principles and Applications for DNA Amplification, H. Erlich, ed., Stockton Press, Chapter 6, pp. 61–70).

Manipulations of the recombinant chymase may also be made at the protein level. Included within the scope of the invention are recombinant chymase fragments or other derivatives or analogs which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

In a specific embodiment, the recombinant chymase derivative is a chimeric, or fusion, protein comprising a chymase or fragment thereof fused to a non-chymase amino acid sequence. In one embodiment, such a chimeric protein is produced by recombinant expression of a nucleic acid encoding the protein (comprising a chymase-coding sequence joined in-frame to a non-chymase coding sequence). Such a chimeric product can be made by ligating the appropriate nucleic acid sequences encoding the desired amino acid sequences to each other by methods known in the art, in the proper coding frame, and expressing the chimeric product by methods commonly known in the art. In a specific embodiment, a chimeric nucleic acid encoding a mature chymase with a heterologous signal sequence is expressed such that the chimeric protein is expressed and processed by the cell to the mature chymase. As another example, and not by way of limitation, a recombinant molecule can be constructed according to the invention, encoding a fusion protein comprising an antibody molecule, or binding domain thereof, fused to the carboxy-terminus of chymase, so as to permit targeting of the chymase to the in vivo antigen recognized by the antibody molecule. Likewise, chimeric genes comprising portions of chymase fused to any heterologous protein-encoding sequences may be constructed. A particular example of a chymase fusion protein is presented in Section 6 infra.

5.7. Assays of Recombinant Chymase, and Chymase Derivatives and Analogs

The functional activity of recombinant chymase, and chymase derivatives and analogs can be assayed by various methods.

For example, in one embodiment, where one is assaying for the ability to bind or compete with wild-type chymase for binding to anti-chymase antibody, various immunoassays known in the art can be used, including but not limited to competitive and noncompetitive assay systems using techniques such as the techniques for screening antibodies described in Section 5.5, supra.

The invention further provides assays for chymase catalytic, i.e., proteolytic, activity. In a preferred embodiment, chymase activity is detected in a standard protease assay with a chromogenic substrate, such as succinyl-L-PhePro-Phe-p-nitroanilide, or other peptide sequences with aromatic residues at the P1 position (the $P_1$—$P_1$, bond in the reactive center of a serine protease substrate is cleaved by the protease (see, e.g., Carrell, 1988, Nature 331:478–479). In a specific example, infra, assays for chymase activity are carried out in cuvettes containing 80 mg/ml of chromogenic substrate, in 30 mM Tris-HCl, pH 8.0, 1M NaCl. The assay is initiated by adding protein, and absorbance is monitored as a function of time. The yield of proteolytically active chymase can be determined from the value of specific activity (absorbance units/mg/min at 37° C.; Caughey et al., 1988, Biochem. Biophys. Acta 952:142–144), and from the slope of the absorbance versus time plot.

Other chymase activity assays include but are not limited to assays of stimulation of serous cell secretion, and cleavage of epithelial cell surface glycocalyx (see Nadel, 1989, Drugs 37 (Suppl. 1):51–55).

The enzymatic assays for chymase activities can also be used to test chymase inhibitors. Inhibitors of chymase catalytic (protease) activity will inhibit activity in the assays described above. The effective concentration of inhibitor to inhibit chymase activity can be measured. Clinically effective chymase inhibitors can inhibit chymase activity in the range of 1 to 100 nM, preferably less than 20 nM, although inhibitors that inhibit at higher concentrations are also of interest.

In another embodiment, chymase activity can be detected as the ability to bind the chymotrypsin inhibitor alpha-1-antichymotrypsin. Chymase is also characterized by being inhibited by soybean trypsin inhibitor but not by aprotinin.

Other methods will be known to the skilled artisan and are within the scope of the invention.

The invention will be further clarified by the following examples, which are intended to be purely exemplary of the invention.

6. EXAMPLE: EXPRESSION OF A CHYMASE FUSION PROTEIN IN *E. coli*

6.1. Materials and Methods

6.1.1. Reagents

Thermostable DNA polymerase from Thermus aquaticus (Taq) was obtained from Perkin-Elmer-Cetus and Promega. T4 DNA ligase was obtained from New England Biolabs. Purified dog chymase has been described previously (Caughey et al, 1988, Biochem. Biophys. Acta 952:142–149). A rabbit anti-dog chymase polyclonal antiserum was prepared against dog chymase using standard procedures. All other enzymes and HPLC-purified deoxynucleoside triphosphates (dNTPs) were obtained from Pharmacia. Human placental cDNA was purchased from Clontech Laboratories, Inc., the maltose binding protein (MBP) fusion expression vector, pmal-c, was obtained from New England Biolabs, and Qiagen DNA purification columns were purchased from Qiagen, Inc. *Escherichia coli* strain XL1-blue was obtained from Stratagene. Acrylamide and succinyl-L-PheProPhe-'p-nitroanilide were purchased from Sigma. Low melting point agarose (SeaPlaque GTG) was obtained from FMC BioProducts. Deoxyoligonucleotide (oligo) primers were obtained from Synthecell Corporation.

6.1.2. Polymerase Chain Reaction (PCR) Assays

The primers (SEQ ID NO:7–10) in Table I were used for PCR:

TABLE I

| PRIMERS USED FOR PCR | |
|---|---|
| 5' primer 1 (Seq ID No: 7) | 5'GCTTCTGACTACAAGGACGACGATGACAAGATCATCGGGGGCACAGAA3' |
| 5' primer 2 (Seq ID No: 8) | 5'ATGATATTCCTTACCACCCTCCCTCTCTTTTGGATAATGATTTCAGCTTCTGACTAC3' |
| 5' primer 3 (Seq ID No: 9) | 5'ATCATCGGGGGCACAGAATGC3' |
| 3' primer (Seq ID No: 10) | 5'AATCTAGATTAATTTGCCTGCAGGAT |

PCR reactions contained 10 mM Tris-HCl, pH 8.4, 50 mM KCl, 1.5 mM MgCl$_2$, 100 µg gelatin/ml, all four dNTPs at 200 µM each, 100 pmoles of each primer, and 2.5 units of Taq polymerase (Perkin-Elmer-Cetus) in a reaction volume of 50–100 µl. First round PCR was carried out on 1 ng of placental cDNA template as follows: one minute at 94° C. for one cycle and 40 cycles of one minute at 94° C., one minute at 50° C., and 1.5 minutes at 72° C. Excess primers, dNTPs, and salts were removed by exclusion chromatography through Chromospin-100 spin columns (Clontech Labs, Inc.) equilibrated against 10 mM Tris-HCl, pH 8.4, 0.1 mM EDTA. Second stage PCR reactions containing first round product as a template, with 5' primer 2 replacing 5' primer 1, were performed under similar conditions for 30 cycles. Screening of *Escherichia coli* colonies by PCR was done as described above except that template DNA was derived from intact *Escherichia coli* cells added directly to the reaction mix; Taq polymerase from Promega was used in these screening reactions.

6.1.3. Gel Electrophoresis

Agarose and non-denaturing polyacrylamide gel electrophoresis (PAGE) was carried out in TBE buffer using standard procedures (Maniatis et al., 1982, Molecular Cloning: A laboratory Manual, Cold Spring Harbor Press). SDS-PAGE was carried out as described (Augsubel et al., 1989, Short protocols in molecular biology, John Wiley & Sons: New York).

6.1.4. Preparation of PCR Products and Vector DNAs for Cloning

PCR products were desalted by exclusion chromatography and treated with DNA polymerase I of *E. coli* (Klenow fragment) to remove the extra nucleotide(s) added to the 3' termini of DNA by Taq DNA polymerase (Clark, 1988, Nucl. Acids. Res. 16:9677–9686). Klenow reactions contained 10 mM Tris-HCl, pH 7.5, 50 mM NaCl, 10 mM MgSO$_4$, 1 mM dithiothreitol, all four dNTPs at 100 µM each, and 1 unit of enzyme. The sample was incubated for 30 minutes at room temperature followed by heat inactivation of the polymerase (10 minutes at 70° C.). XbaI (30 units) was added to the reaction, which was then incubated at 37° C. for 2–3 hours. The reaction was terminated by the addition of EDTA to 20 mM. The restricted DNA was electrophoresed through a 4% polyacrylamide gel and the appropriate band was identified by ethidium bromide fluorescence, eluted from the gel overnight, and recovered by ethanol precipitation. About 5 µg of the pmal-c vector DNA was restricted with StuI (10 units) and XbaI (15 units) in buffer provided by the supplier at 37° C. for 3 hours. Linear DNA was purified by electrophoresis through a low-melting point agarose gel (0.8%) and recovered by phenol extraction followed by ethanol precipitation.

6.1.5. DNA Ligation and *E. coli* Transformation

A seven-fold molar excess of gel-purified PCR product (about 100 ng) was ligated overnight at 17° C. to linear vector DNA (about 120 ng) with 200 units of T4 DNA ligase in buffer provided by the supplier. The resulting plasmid was named pMBPCHY. The ligation product was then transformed into competent *Escherichia coli* (XL1-Blue; Stratagene) and ampicillin resistant colonies were isolated by plating on LB-ampicillin plates.

6.1.6. DNA Sequence Analysis

Plasmid DNA for sequence analysis was isolated from overnight cultures by alkaline lysis and purification on Qiagen columns following the protocol recommended by the supplier. Sequence analysis was carried out on double stranded plasmid DNA with Sequenase and $^{35}$S-dATP essentially as described by the enzyme supplier (United States Biochemical Corporation; Sequenase version 2.0)

6.1.7. Expression and Purification of Fusion Proteins

Expression and purification of recombinant protein was carried out essentially as recommended by the supplier of the pmal-c vector (New England Biolabs). Briefly, overnight cultures of *Escherichia coli* XL1-blue containing the plasmid construct were diluted 1:100 into LB medium supplemented with 0.2% glucose plus 100 µg ampicillin/ml, and grown to a density of ~2×10$^8$ cells/ml (A$_{600}$=0.5). An aliquot of cells was removed, pelleted, and resuspended in SDS-PAGE sample buffer for analysis on an SDS-PAGE gel (uninduced cells). IPTG (0.3 mM) was added to the remaining cells which were incubated in a rotary shaker at 37° C. for 2 hours. Aliquots of induced cells were pelleted and prepared for electrophoretic analysis.

Large scale preparation of fusion protein was carried out under similar induction conditions with larger culture volumes (typically 0.5 liter). Cells were harvested by centrifugation, resuspended in lysis buffer (10 mM sodium phosphate buffer, pH 7.0, 30 mM NaCl, 10 mM β-mercaptoethanol, 10 mM EDTA, 10 mM EGTA, 0.25% Tween), subjected to one cycle of freezing (−70° C.) and thawing (0° C.), and lysed by sonication. Lysates were adjusted to 0.5M NaCl and pelleted by centrifugation (9000×g, 20 min). The fusion protein was recovered in the insoluble fraction (determined in preliminary experiments), resolubilized in 8M urea, and dialyzed overnight at 4° C. against 10 mM sodium phosphate buffer, pH 7.0. After centrifugation, soluble fusion protein was recovered in the supernatant fraction and mixed with 20 ml of amylose affinity resin in binding buffer (10 mM sodium phosphate, pH 7.0, 0.5M Nacl, 10 mM β-mercaptoethanol, 1 mM EGTA). Following an overnight incubation at 4° C., resin-bound protein was recovered by centrifugation, washed twice with binding buffer, and eluted from the resin with binding buffer containing 10 mM maltose. Purified protein was dialyzed against 20 mM Tris-HCl, pH 8.0, 100 mM NaCl, concentrated (Amicon centriprep) to ~1 mg/ml, and stored at 4° C.

The fusion protein was cleaved with Factor Xa. Cleavage reactions were carried out at a Factor Xa:MBP-chymase ratio of 1% (w/w) in 20 mM Tris-HCl, pH 8.0, 100 mM NaCl, 2 mM $CaCl_2$. Samples were incubated overnight (~18 hr) at room temperature.

6.1.8. Assays for Chymase Activity

Assays for chymase activity were carried out in cuvettes, which contained, in 1 ml, 80 μg of the chromogenic substrate succinyl-L-PheProPhe-p-nitroanilide in 30 mM Tris-HCl, pH 8.0, 1M NaCl. Samples were placed in a spectrophotometer and set to zero absorbance. The assay was initiated by mixing in approximately 10 μg of protein and absorbance at 405 nm was monitored as a function of time. Chymase activity was determined from the specific activity (110 absorbance units/mg/min at 37° C.; Caughey et al., 1988, Bioch. Biophys. Acta 952:142–149) and the slope of the absorbance vs. time plot.

6.2. Results and Discussion

6.2.1. Isolation of DNA Sequences Encoding Human Chymase

Oligonucleotide primers complementary to the human chymase cDNA sequence (Caughey et al., 1991, J. Biol. Chem. 266:12956–63) were used to amplify by PCR a 681 base pair fragment encoding the chymase catalytic domain (FIG. 1). The 5' primer used for the first round of PCR (5' primer 1; SEQ ID NO:7) codes for a portion of the myelin associated glycoprotein (MAG) leader sequence (Fujita et al., 1989, Biochem. Biophys. Res. Commun. 165:1162–1169), the 8 amino acid FLAG epitope/enterokinase cleavage site (Hopp et al., 1989, Biotechniques 7:580–589), and the first 18 nucleotides of chymase starting at the isoleucine (Ile) residue corresponding to the free amino terminus of the mature protein (Schecter et al., 1990, J. Immunol. 145:2652–2661; Urata et al., 1990, J. Biol. Chem. 265:2234–57). The 3' primer (SEQ ID NO:10) incorporates an XbaI restriction site to facilitate cloning. The 5' primer 2 (SEQ ID NO:8) codes for the remainder of the MAG leader sequence and shares a 12 nucleotide overlap with 5' primer 1 (See Table I). These primers were designed to isolate, after two stages of PCR, the catalytic domain of chymase fused to the MAG leader sequence along with the FLAG epitope to facilitate protein export and purification in a mammalian expression system (see below).

The first stage PCR reaction amplified a single band of appropriate size from human placental cDNA (FIG. 2). This DNA was then used as a template for a second round of PCR to complete the addition of the MAG leader sequence. DNA from the second stage PCR was examined by restriction analysis for the presence of diagnostic BamHI, HindIII, and PvuIII restriction sites. All three sites were present in the PCR product, suggesting that the PCR reaction had successfully amplified human chymase cDNA. The identity of the gene encoded by this DNA fragment as chymase was subsequently confirmed by DNA sequence analysis of cloned inserts (see below).

6.2.2. Cloning of Amplified Chymase cDNA

Initial attempts to clone the second stage PCR product into a mammalian expression vector (RC/CMV; Invitrogen) generated plasmids that were unstable and rapidly accumulated deletions and/or insertions within the cloned insert. A new 5' primer (5' primer 3; SEQ ID NO:9) that starts at the beginning of the chymase catalytic domain was used with the 3' primer to screen colonies for the presence of the insert by PCR. Screening of colonies that resulted from transformation of the ligation mixture into several different *Escherichia coli* host strains yielded a DNA product of the correct size along with additional PCR products; however, subsequent expansion of individual clones yielded only plasmid DNA that had undergone rearrangement. The PCR product of appropriate size that resulted from these screening efforts was treated as described in Materials and Methods and cloned into the pmal-c MBP expression vector in an effort to obtain stable DNA clones and a recombinant fusion protein to be used as an immunogen for antibody production.

6.2.3. Identification of MBP-Chymase Expressing Clones

Seven clones were identified by PCR as having chymase gene inserts of the appropriate size (FIG. 3). Six of these clones produced a recombinant fusion protein of appropriate size following IPTG induction as judged by SDS-PAGE analysis of total cell extracts; one clone produced a smaller (inducible) protein (FIG. 4). Only six clones were analyzed on the gel shown in FIG. 4; clone number 7 also produced a fusion protein of appropriate size. The nucleotide sequences of DNA from two independent clones, shown in FIG. 5, differed slightly from the reported sequence for human chymase (Caughey et al., 1991, J. Biol. Chem. 266:12956–12963; Urata et al., 1991, J. Biol. Chem. 266:17173–17179). Clone 7 contains two synonymous substitutions and one A to G transition that results in a lysine to glutamic acid change at position 204 (corresponding to residue 221 in chymotrypsinogen) in the peptide sequence. Clone 3 has one synonymous change in addition to A to G and T to C transitions that result in Lys to Glu (at residue 96=residue 109 in chymotrypsinogen) and Ser to Pro (residue 50=residue 63 in chymotrypsinogen) mutations respectively. The origin of these mutational changes is unknown; they may represent PCR or cloning artifacts. Alternatively, one or more of these changes could represent allelic variation in the chymase gene. In this context, it is of interest that one of the changes identified in clone 3 creates a new StuI restriction site (shown underlined in FIG. 5).

A fusion protein containing a wild type chymase amino acid sequence was constructed by ligating the large (5' end) fragment obtained by digesting a full length PCR fragment amplified from clone 7 DNA with StuI and XbaI to the 230 base pair (3' end) StuI/XbaK fragment derived from a PCR fragment amplified from clone 3 DNA. Sequence analysis of the reconstructed clone (designated MBP-chymase) confirmed that the fusion protein expressed by this clone contained the wild type amino acid sequence.

6.2.4. Purification and Characterization of Recombinant MBP-Chymase

Recombinant MBP-chymase was initially isolated from IPTG-induced cells in an insoluble form and, after resolubilization, purified by amylose affinity chromatography. The protein migrated on SDS-PAGE gels as a band corresponding to an apparent $M_r$ of approximately 67 kd (FIG. 6, Lane 3), as expected for MBP (42 kd) fused to chymase (25 kd). MBP-chymase had no detectable proteolytic activity when assayed on the chromogenic substrate, succinyl-L-PhePro-Phe-p-nitroanilide. Chymase purified from dog mastocytoma cells (Caughey et al., 1988, Bioch. Biophys. Acta 952:142–149) was used as a positive control for the assay.

6.2.5. Cleavage of MBP-Chymase With Factor Xa

The pmal-c expression vector incorporates a cleavage site for the specific protease Factor Xa (Nagia et al., 1987, Methods Enzymol. 153:461–481) adjacent to the cloned gene. This allows the MBP portion of the fusion protein to be proteolytically cleaved from MBP-chymase. Cleavage of MBP-chymase with Factor Xa generated three major products on SDS-PAGE gels, the 42 kd MBP and two fragments of approximately 25 kd (FIG. 6, Lane 7). Chymase generated by Factor Xa cleavage was detectable on a Western blot with a polyclonal antibody made against active dog chymase (FIG. 7), suggesting that the recombinant human enzyme expressed in *Escherichia coli* shares one or more antigenic determinants with the dog enzyme.

6.3. Conclusion

A cDNA encoding the catalytic domain of human mast cell chymase was fused to DNA sequences encoding the maltose binding protein of *Escherichia coli*, yielding expression of a fusion protein that was immunologically cross-reactive with polyclonal antiserum directed against enzymatically active dog chymase. The fusion protein showed no detectable proteolytic activity on a synthetic chymase substrate. Free chymase, released by Factor Xa cleavage of the fusion protein, was also inactive as a protease. Since the fusion protein was expressed in the cytoplasm of *Escherichia coli*, formation of the three disulfide bridges found in native chymase (Caughey et al., supra; Remington et al., 1988, Biochem. 27:8097–8105) is unlikely to occur. As shown in Sections 7 and 8, infra, active, recombinant chymase can be produced if the enzyme is renatured under conditions that permit disulfide bond formation. The recombinant chymase fusion protein is also useful as an immunogen for polyclonal and monoclonal antibody production.

7. EXAMPLE: RECOVERY OF ENZYMATICALLY ACTIVE RECOMBINANT HUMAN CHYMASE

7.1. Methods

MBP-chymase fusion protein, recovered in the insoluble fraction from cell extracts, was resuspended in lysis buffer containing β-mercaptoethanol and 8M urea. After sonication to completely resuspend the pellet, the sample was dialyzed against 10 mM sodium phosphate buffer, pH 7.2 overnight. Insoluble material was removed by centrifugation and the fusion protein was then purified by amylose affinity chromatography as above. The fusion protein was eluted from the resin with maltose and dialyzed against 20 mM Tris-HCl, pH 8.0, 100 mM NaCl. The protein was then exchanged into reducing buffer #1 (0.1M Tris-HCl, pH 8.7, 1 mM EDTA, 6M guanidine-HCl, 0.15M NaCl, 0.3 M reduced glutathione) and incubated at room temperature for 2 hours. The sample was diluted 100-fold into oxidizing buffer #2 (0.1 Tris-HCl, pH 8.0, 1 mM EDTA, 0.15M NaCl, 0.3 mM oxidized glutathione), stirred for 2–48 hr at room temperature, and concentrated 100-fold to 285 μg/ml by ultrafiltration using an Amicon stirred flow cell. Factor Xa cleavage reactions were carried out at room temperature overnight. Ten μl samples were periodically removed and assayed for chymase activity in the presence or absence of various proteinase inhibitors. Several control experiments were also performed as described below.

7.2. Results

Cleavage of the refolded fusion protein by Factor Xa resulted in the release of enzymatically active, recombinant human chymase as measured by hydrolysis of the chymase substrate. The activity released by Factor Xa increased with time from 2.7 μg/ml at 2 hours to 4.6 μg/ml at 5 hours and remained at the latter level for up to 24 hours. The yield of active chymase was low; only about 1.6% of the starting fusion protein was converted to an active product even though essentially all of the fusion protein was cleaved by Factor Xa (as determined by SDS-PAGE).

Several control experiments were performed to verify that the observed enzymatic activity was indeed due to chymase. First, Factor Xa alone had no detectable activity on the chymase substrate. Second, incubation of the fusion protein in the absence of Factor Xa did not result in detectable enzymatic activity. The latter result confirms that release of active chymase is dependent upon Factor Xa cleavage of the fusion protein and that the uncleaved (inactive) protein does not undergo autocatalysis. Third, the inhibitor profile of recombinant human chymase was qualitatively similar to that of human heart chymase (Table II). In summary, we have produced detectable amounts of enzymatically active, recombinant human chymase by proteolytically cleaving an inactive precursor fusion protein. As shown in Section 8, infra, the yield of active chymase was increased by optimizing the conditions used to refold and cleave the fusion protein.

TABLE II

INHIBITOR PROFILE OF RECOMBINANT HUMAN CHYMASE

| | % Residual Activity | |
|---|---|---|
| Inhibitor | Recombinant Enzyme | Heart Chymase[6] |
| None | 100 | 100 |
| PMSF[1] 1 mM | 0 | 0 |
| TPCK[2] 100 μM | 0 | — |
| 1 mM | — | 30 |
| SBTI[3] 1 μM | — | 0 |
| 25 μM | 0 | — |
| 100 μM | — | 0 |
| LEU[4] 10 μM | 100 | 106 |
| APRO[5] 10 μM | 100 | 107 |

[1]PSMF = phenylmethylsulfonyl fluoride
[2]TPCK = p-tosyl-L-phenylalanine chloromethyl ketone
[3]SBTI = soybean trypsin inhibitor
[4]LEU = leupeptin TABLE II-continued

INHIBITOR PROFILE OF RECOMBINANT HUMAN CHYMASE

| | % Residual Activity | |
|---|---|---|
| Inhibitor | Recombinant Enzyme | Heart Chymase[6] |

[5]APRO = aprotinin
[6]Data from Urata et al., 1990, J. Biol. Chem. 265:22348-22357

8. EXAMPLE: OPTIMIZATION OF REFOLDING CONDITIONS FOR RECOVERY OF ENZYMATICALLY ACTIVE, RECOMBINANT HUMAN CHYMASE

8.1. Methods

MBP-chymase fusion protein, recovered in the insoluble fraction from cell extracts, was resuspended in lysis buffer (20 mM Bis-Tris, pH 7.2, 10 mM β-mercaptoethanol, 10 mM EDTA, 10 mM EGTA) containing 6 M urea and loaded onto a Mono-Q anion exchange FPLC column. The denatured fusion protein was eluted from the column with a 0–1M NaCl gradient in lysis buffer plus urea and exchanged into reducing buffer #1 (0.1M Tris-HCl, pH 8.7, 1 mM EDTA, 6M guanidine-HCl, 0.15M NaCl, 0.3M reduced glutathione). After incubation in reducing buffer #1 for 2–16 hr at room temperature, the sample was diluted 100-fold into oxidizing buffer #3 (0.1M Tris-HCl, pH 8.0, 1 mM EDTA, 0.15M NaCl, 0.3 mM oxidized glutathione, 1M ammonium sulfate, 3 mg/ml PEG 3400) and incubated at room temperature for 2–16 hr. The refolded fusion protein was concentrated 100-fold and treated with Factor Xa as before to release the chymase portion of the protein. Assays for chymase activity were carried out as described previously.

8.2. Results

Denatured, purified fusion protein eluted from the Mono Q column at ~0.5 M NaCl and was essentially homogeneous at this stage. Enzymatically active chymase was recovered in 40–60% yield after the above refolding protocol. The yield of active enzyme was estimated as the ratio of the amount of active chymase protein present after Factor Xa cleavage (determined from the activity measurement as described previously) to the total amount of fusion protein present prior to the addition of Factor Xa, correcting for the fact that chymase represents only 37% of the mass of the intact fusion protein. An extensive evaluation of alternative refolding protocols was also carried out and the procedure described above was found to be optimal. A number of parameters were found to significantly affect the recovery of active chymase including temperature (room temperature was better than 4° C.), method of buffer exchange from reducing buffer #1 to oxidizing buffer #3 (rapid dilution was better than dialysis), and the particular chaotropic agent added to reducing buffer #1 (guanidine-HCl was better than urea). The urea solubilization step prior to the Mono-Q column was needed for optimal activity, as was the inclusion of ammonium sulfate and PEG 3400 in oxidizing buffer #3 (see Section 8.1., supra). Alteration of any of these steps generally reduced the yield of active chymase to less than 10%.

9. DEPOSIT OF MICROORGANISMS

Bacteria strain XL1-Blue containing plasmid pMBPCHY was deposited on Jul. 24, 1992 with the American Type Culture Collection (ATCC), 12301 Parklawn Drive, Rockville, Md. 20852, under the provisions of the Budapest Treaty on the International Recognition of the Deposit of Microorganisms for the Purposes of Patent Procedures, and assigned ATCC Accession No. 69037.

The present invention is not to be limited in scope by the microorganism deposited or the specific embodiments described herein since such embodiments are intended as but single illustrations of one aspect of the invention and any microorganisms which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

It is also to be understood that all base pair sizes given for nucleotides are approximate and are used for the purpose of description.

Various references are cited herein, the disclosures of which are incorporated by reference herein in their entirety.

---

What is claimed is:

1. A method for producing a chymase comprising the following steps in the stated order:
  (a) culturing a host cell which contains a recombinant DNA molecule comprising a first nucleotide sequence encoding a fusion protein, which fusion protein comprises at least a portion of a non-chymase protein joined via a peptide bond to a chymase having an amino acid sequence selected from the group consisting of SEQ ID NO:2, SEQ ID NO:4, and SEQ ID NO:6; and a second nucleotide sequence comprising a promoter, which promoter controls expression of the first nucleotide sequence, whereby the fusion protein is expressed by the cultured cell;
  (b) recovering the fusion protein expressed by the cultured cell;
  (c) refolding the fusion protein;
  (d) cleaving the portion of the non-chymase protein from the chymase; and
  (e) recovering the chymase;
  whereby the recovered chymase is proteolytically active, in which the refolding step comprises the following steps in the stated order:
    (i) incubating the protein in a reducing buffer; and
    (ii) incubating the protein in an oxidizing buffer.

2. The method of claim 1 in which the refolding step further comprises solubilizing the fusion protein in a denaturant and purifying the solubilized fusion protein prior to the incubation of step (i).

3. The method of claim 1 in which the oxidizing buffer comprises a protein stabilizing agent.

4. The method of claim 1 in which the oxidizing buffer comprises a chaotropic agent.

5. The method of claim 1 which further comprises diluting the reducing buffer in step (i) into the oxidizing buffer in step (ii).

6. A method for producing a proteolytically active chymase, comprising the following steps in the stated order:
  (a) culturing a host cell which contains a recombinant DNA molecule comprising a first nucleotide sequence encoding a fusion protein, which fusion protein comprises a chymase having an amino acid sequence selected from the group consisting of SEQ ID NO:2, SEQ ID NO:4, and SEQ ID NO:6 and at least a portion of a non-chymase protein, wherein the non-chymase protein is joined via a peptide bond to the amino terminus of the chymase; and a second nucleotide sequence comprising a promoter, which promoter controls expression of the first nucleotide sequence, whereby the fusion protein is expressed by the cultured cell;
  (b) recovering the fusion protein expressed by the cultured cell;
  (c) solubilizing the fusion protein in urea;

(d) purifying the solubilized fusion protein by high performance anion exchange chromatography;
(e) incubating the purified fusion protein in a reducing buffer comprising guanidine-HCl;
(f) rapidly diluting the fusion protein in an oxidizing buffer, which oxidizing buffer comprises ammonium sulfate and PEG-3400;
(g) incubating the fusion protein in the oxidizing buffer;
(h) cleaving the portion of the non-chymase protein from the chymase; and
(i) recovering the chymase; whereby the chymase is proteolytically active.

* * * * *